United States Patent
Choi et al.

(10) Patent No.: US 8,306,308 B2
(45) Date of Patent: Nov. 6, 2012

(54) METHOD FOR OPTICALLY DETECTING SURFACE DEFECT OF ROUND WIRE ROD

(75) Inventors: Se Ho Choi, Pohang (KR); Ho Mun Bae, Pohang (KR); Hwa Won Hwang, Pohang (KR); Chang Hyun Park, Pohang (KR)

(73) Assignee: POSCO, Pohang (KR)

( * ) Notice: Subject to any disclaimer, the term of this patent is extended or adjusted under 35 U.S.C. 154(b) by 309 days.

(21) Appl. No.: 12/675,405

(22) PCT Filed: Aug. 28, 2008

(86) PCT No.: PCT/KR2008/005052
§ 371 (c)(1),
(2), (4) Date: Feb. 26, 2010

(87) PCT Pub. No.: WO2009/028883
PCT Pub. Date: Mar. 5, 2009

(65) Prior Publication Data
US 2010/0246974 A1 Sep. 30, 2010

(30) Foreign Application Priority Data
Aug. 28, 2007 (KR) .................. 10-2007-0086464

(51) Int. Cl.
*G06K 9/00* (2006.01)
*G01B 11/02* (2006.01)
*G01B 11/24* (2006.01)
*G01B 11/30* (2006.01)

(52) U.S. Cl. ..................... 382/141; 356/601; 356/635

(58) Field of Classification Search ........... 382/141–152
See application file for complete search history.

(56) References Cited

U.S. PATENT DOCUMENTS

| | | | | |
|---|---|---|---|---|
| 4,095,905 A | * | 6/1978 | Kuni et al. ................. | 356/430 |
| 4,223,346 A | * | 9/1980 | Neiheisel et al. ........... | 348/131 |
| 4,226,539 A | * | 10/1980 | Nakagawa et al. .......... | 356/445 |
| 4,734,766 A | * | 3/1988 | Shiozumi et al. ........... | 382/141 |
| 4,759,072 A | * | 7/1988 | Yamane et al. ............. | 382/152 |
| 5,363,901 A | * | 11/1994 | Bjornestol et al. .......... | 164/451 |
| 6,859,285 B1 | | 2/2005 | Chang | |
| 6,950,546 B2 | * | 9/2005 | Chang et al. ............... | 382/141 |
| 8,143,885 B2 | * | 3/2012 | Chang et al. ............... | 324/240 |
| 2006/0002605 A1 | | 1/2006 | Chang et al. | |
| 2007/0246643 A1 | | 10/2007 | Fardeau | |
| 2008/0296336 A1 | | 12/2008 | Kim et al. | |

FOREIGN PATENT DOCUMENTS

| | | |
|---|---|---|
| CA | 2051032 A1 | 3/1992 |
| CN | 1584179 A | 2/2005 |
| EP | 1508797 A1 | 2/2005 |
| EP | 1774299 A1 | 4/2007 |

(Continued)

*Primary Examiner* — Gregory J Toatley
*Assistant Examiner* — Jarreas C Underwood
(74) *Attorney, Agent, or Firm* — The Webb Law Firm

(57) ABSTRACT

A device and method can optically detect a defect of a round wire rod to be tested, and particularly, remotely detect the defect without contact in real-time. The device includes a lighting device for emitting circular surface light to the round wire rod; an optical sensor for generating an optical signal by receiving the light reflected from the round wire rod, which is being transported, and converting the optical signal into an image signal; and a signal-processing unit for acquiring surface information of the round wire rod by receiving the image signal from the optical sensor.

1 Claim, 24 Drawing Sheets

FOREIGN PATENT DOCUMENTS

| | | |
|---|---|---|
| JP | 6102194 A | 4/1994 |
| JP | 06249794 A | 9/1994 |
| JP | 7148656 A | 6/1995 |
| JP | 2004163176 A | 6/2004 |
| JP | 2005010036 A | 1/2005 |
| KR | 20020050832 A | 6/2002 |
| KR | 20070056353 A | 6/2007 |

* cited by examiner

Original Image | Second Differentiation | Threshold Applied | Morphology

METHOD FOR OPTICALLY DETECTING SURFACE DEFECT OF ROUND WIRE ROD

BACKGROUND OF THE INVENTION

1. Field of the Invention

The present invention relates to a device and method for optically detecting a surface defect of a round wire rod in real-time and without contact. The device and method can detect the surface defect using an optical sensor, in which the surface defect occurs on the wire rod in a process of manufacturing the wire rod through rolling, drawing and extrusion.

2. Description of Related Art

Technologies for detecting a surface defect of round wire rods include ultrasonic test, Magnetic Flux Leakage (MFL), Magnetic Particle Inspection (MPI), eddy current inspection, optical inspection and so on.

The ultrasonic test is a method that determines whether or not a bar or wire rod has a surface defect by transmitting a surface ultrasonic wave from an ultrasonic generator to the wire rod subjected to surface defect detection, receives an ultrasonic wave signal reflected from the wire rod, and analyzes the reflecting ultrasonic wave signal. The ultrasonic test is excellent for detecting non-continuous surface defects such as a crack formed in the direction perpendicular to the transmission direction of the ultrasonic wave. However, it is not effective for detecting some surface defects, which are formed along the transmission direction of the ultrasonic wave or are followed by a smooth shape change. The ultrasonic test can hardly transmit ultrasonic energy to the whole surface of a circular object to be tested (hereinafter, referred to as "test object"). In particular, the efficiency of transmitting an ultrasonic wave from the ultrasonic generator to the test object is poor when the test object has a large surface roughness, is accompanied with vibration, is hot, or is being transmitted.

The magnetic flux leakage (MFL) can excellently detect cracks in or under the surface of ferromagnetic metal. The detection performance of the MFL is excellent for fine cracks even if surface roughness is very large, but is not effective for cracks formed along the direction of a magnetic flux, which is generated on the surface of a ferromagnetic object, or when a defect has a smooth edge.

The principle of the MFL is as follows: When an air gap is formed in a crack of a test object or impurities are accumulated in the crack, permeability characteristics become different from those of a ferromagnetic body. While the magnetic flux is continuously formed to be parallel to the surface of the test object when the surface has normal conditions, a magnetic flux leaks in the direction perpendicular to the surface when there is a permeability difference. Then, a defect such as a crack is detected by measuring a magnetic flux leakage using a magnetic flux leakage sensor.

The MFL may cause some problems when applied to a round bar that is hot and is transported at a high speed.

Firstly, since the magnetic flux leakage sensor is not stable with temperature changes, the stability of the magnetic flux leakage sensor is not maintained when applied to a hot material.

Secondly, it is very difficult to generate a magnetic flux on the surface of a predetermined portion of a steel member that is moving at a high speed.

Thirdly, a magnetic flux leakage signal detected by the magnetic flux leakage sensor is inverse proportional to square of distance. When a wire rod, which is being transported at a high speed, vibrates, a pseudo defect occurs since it is difficult to discriminate a defect signal from a vibration signal.

Fourthly, a constant distance has to be maintained between the surface of a test object and the sensor in order to detect a defect of a round bar. It is also required to arrange a sensor system in circle. Here, a sensor head has to be replaced whenever the diameter of the round wire bar changes. Since products having a variety of diameters are manufactured on a single manufacturing line, an operation of replacing the sensor head in the manufacturing line according to changes in diameter causes a considerably large amount of load.

The Magnetic Particle Inspection (MPI) is very similar to the MFL in a process of forming a magnetic flux leakage when a test object has a defect in the surface. The MPI directly measures the magnetic flux leakage formed in the defect of the test object using a sensor capable of detecting the magnetic flux leakage and distributes magnetic particles coated with fluorescent material on the test object in order to more clearly clarify information on the formed magnetic flux leakage. An area of the test object having the magnetic flux leakage attracts the magnetic particles using a magnetic attractive force, but a normal area of the test object does not attract the magnetic particles. Since the fluorescent material, which sensitively reacts with ultraviolet rays, is coated on the magnetic particles for a visual effect, it is possible to acquire the geometry of the defect by emitting ultraviolet light. Unlike the ultrasonic test or the MFL, the MPI can acquire the distribution of magnetic particles corresponding to the geometry of the defect so as to classify the defect based on its geometry information. Since the MPI detects a defect using an optical sensor instead of the magnetic flux leakage sensor, it can overcome some drawbacks of the MFL related with vibration or the magnetic flux leakage sensor and thus is widely used. However, the MPI is generally used when the test object has a temperature 70° or less due to limited temperature characteristics of the fluorescent magnetic particles. Since the MPI requires an additional work such as magnetic particle inspection and forming of a magnetic field on the test object, it is difficult to apply the MPI to a continuous manufacturing line such as a rolling line.

The eddy current inspection is a technique using electromagnetic characteristics of metal, and is applicable to a material such as a hot bar, which is continuously manufactured using an eddy current sensor having a relatively short response time. The eddy current inspection has a drawback in that defects may increase when the test object vibrates since the eddy current sensor has to be arranged very close to the test object as in the sensor arrangement of the MFL. Since a defect of the signal having a predetermined threshold or more is qualitatively determined by analyzing an analog signal generated by the eddy current sensor, it is difficult to make a quantitative determination on for example the size, length and height of the defect. In particular, some defects having a specific geometry are not easily detectable. In general, the eddy current inspection is widely used to statistically analyze overall changes in test objects according to changes in manufacturing conditions or times rather than detecting respective defects and evaluating characteristics.

The optical inspection is generally divided into two methods. The first method is to discriminate a defective portion from a normal portion by directly receiving light, which is spontaneously emitted from a hot test object. The second method is to discriminate a defective portion from a normal portion by emitting light from an external light source to a hot test object and receiving light reflected from the test object.

1. First Method

Referring to FIG. 1, light energy radiated from the surface of a hot round wire rod 2 is received using an optical sensor 1 and a defect is detected by discriminating between a sensor signal from a normal portion and a sensor signal from an abnormal portion.

Emissivity is the level of energy radiated outwards from the surface of a material. The emissivity of hot metal is varied according to the temperature, surface characteristics and types of metal. When metal has a surface defect, its emissivity is varied owing to the difference in roughness, area and surface luminance between a defective portion and a normal portion. The varied emissivity causes the defective portion to emit a different amount of energy from the normal portion. In order to observe the defective portion of the metal surface, on the assumption that the temperature of metal is constant and the construction of the optical sensor is uniform, the difference in emissivity between the defective and normal portions changes the characteristics of light emitted from the round wire rod 2 and influences the output voltage of the optical sensor 1. In particular, factors influencing emissivity include the difference in surface roughness between the defective and normal portions, the difference in components between the defective and normal portions and the difference in temperature between the defective and normal portions.

In the case of using light spontaneously emitted from the round wire rod 2, when the difference in surface luminance between the normal and defective portions is great, the difference in emissivity between the normal and defective portions increases. As excellent characteristics, the power of discrimination of defects can be raised by increasing the difference between the response values of the optical sensor 1. When the emissivity difference between the defective and normal portions is not large or the emissivity of the defective portion does not have predetermined characteristics, the detection method using spontaneous emission is not effective.

2. Second Method

Referring to FIG. 2, the optical inspection method uses light emitted from an external lighting device 3. The external lighting device 3 emits light having wavelength characteristics different from or the same as those emitted from a round wire rod 2. The intensity of light emitted from the lighting device 3 is set to be greater than that emitted from the round wire rod 2.

When light emitted from the lighting device 3 has a wavelength band different from that emitted from the hot round wire rod 2, there is required an optical filter 5 that transmits the light emitted from the lighting device 3 but does not transmit the light emitted from the hot round wire rod 2. The optical filter 5 used can shield radiation energy emitted from the hot round rod 2 and minimize an influence of light emitted from the hot round rod 2 on the optical sensor 1. When the sensitivity of the optical sensor 1 is poor, the intensity of light emitted from the lighting device 3 has to be increased. The arrangement of the lighting device 3 has to be designed according to the surface geometry of the round wire rod 2.

As shown in FIG. 3, when the test object is shaped like a slab, the external lighting device 3 can emit light so as to be uniformly reflected from the surface of the slab 6. This provides uniform signal characteristics to an optical sensor 1 (also referred to as signal detecting sensor) so that defects can be detected from a wide surface area. It can be appreciated that the sensor signals having a substantially uniform magnitude are obtained from the central portion and edge portions along the width direction of the slab 6.

As shown in FIG. 4, in the case where a test object is a round wire rod 2, when external light is emitted from an external lighting device 3, a reflection angle at a reflection point is the same as an incident angle with respect to a normal from the surface. As a result, defect inspection can be performed on only a small area since only a small surface area can reflect light toward an optical sensor 1 (also referred to as signal detecting sensor).

SUMMARY OF THE INVENTION

One or more aspects of the present invention provide a device and method, which can optically detect a defect of a round wire rod to be tested, and particularly, remotely detect the defect without contact in real-time.

According to an aspect of the present invention, the device for optically detecting a defect of a round wire rod may include a lighting device for emitting circular surface light to the round wire rod; an optical sensor for generating an optical signal by receiving light emitted by the lighting device and reflected from the round wire rod, which is being transported, and converting the optical signal into an image signal; and a signal-processing unit for acquiring surface information of the round wire rod by receiving the image signal from the optical sensor.

In an exemplary embodiment of the present invention, the device may further include a speedometer for detecting a transporting speed of the round wire rod.

In another embodiment of the present invention, the speedometer is a laser speedometer.

In a further embodiment of the present invention, the speedometer detects the round wire rod whenever being transported at a predetermined interval and transmits a detection result to the optical sensor.

In an exemplary embodiment of the present invention, the device may further include a guide for restricting a transportation path of the round wire rod.

In another embodiment of the present invention, the guide is configured as circular column surrounding the round wire rod, and has a conical shape at one end thereof.

In a further embodiment of the present invention, the guide is made of stainless steel.

In an exemplary embodiment of the present invention, an angle ranging from 50° to 90° can be defined between a direction in which the optical sensor receives the reflected light from the round wire rod and a transporting direction of the round wire rod.

In an exemplary embodiment of the present invention, an angle ranging from 45° to 65° can be defined between a light-emitting direction of the lighting device and a transporting direction of the round wire rod.

In an exemplary embodiment of the present invention, an angle ranging from 45° to 60° can be defined between a light-emitting direction of the lighting device and a vertical radial direction of the round wire rod.

In an exemplary embodiment of the present invention, the device may further include an optical filter provided under the optical sensor, wherein the optical filter receives the reflected light from the round wire rod, transmits a blue wavelength band to be sent to the optical sensor, and does not transmit an infrared wavelength band.

In another embodiment of the present invention, the optical filter has a center wavelength ranging from 450 nm to 490 nm.

In an exemplary embodiment of the present invention, the device may further include a luminance controller for detecting a current supplied to the lighting device and monitoring light emitted from the supplied current.

In another embodiment of the present invention, the device may further include a server for turning on and off the luminance controller or controlling an operation of the luminance controller via Transmission control protocol/Internet protocol (TCP/IP).

In an exemplary embodiment of the present invention, a plurality of the lighting devices are provided, and the server selectively turns on and off the lighting devices.

In another embodiment of the present invention, the server generates a warning sound when detecting that the lighting device does not have a predetermined level of luminance.

According to another aspect of the present invention, the method for optically detecting a defect of a round wire rod may include the steps of: acquiring an image of the round wire rod from an optical sensor, and filtering the acquired image; performing second-order partial differentiation on a first linear image acquired in the direction perpendicular to a transporting direction of the round wire rod, averaging second-order partial differentiation values of the first linear image, and setting the averaged value as a first threshold; performing second-order partial differentiation on a second linear image acquired in the direction perpendicular to the transporting direction of the round wire rod, and removing the first linear image and accumulating the second linear image if a difference between each second-order partial differentiation value of the first linear image and the first threshold is within a predetermined range; averaging second-order partial differentiation values of the second linear image, and setting the averaged value as a second threshold; performing second-order partial differentiation on a second linear image acquired in the direction perpendicular to the transporting direction of the round wire rod, and repeating zooming of pixels of the second linear image up to a predetermined number of times if a difference between each second-order partial differentiation value of the second linear image and the second threshold is within a predetermined range; and detecting the second linear image pixels as bad pixels if the second linear image pixels are not converted into a single pixel.

According to one or more aspects of the present invention, an image having a predetermined definition can be acquired from an environment in which the transporting speed of a wire rod changes, and thus the length, width, size and defect location can be correctly acquired.

According to one or more aspects of the present invention, an image sensor and the emission angle of an external light source are arranged to produce a dark field, which reduces an influence of surface scales compared a bright field of the related art. Therefore, it is not required to install the device for detecting a defect of wire rods in a place right downstream of rolling.

According to one or more aspects of the present invention, the image sensor and the emission angle of the external light source are arranged to produce double dark fields, and particularly, arranged with respect to the transporting direction and the radial direction of a round wire rod to produce dark fields, respectively. This makes it possible to sensitively detect changes in the edge inclination of a defect both in the transporting direction and in the radial direction of the round wire rod. Accordingly, the defect detection performance of the device for detecting a surface defect is significantly improved over that of the related art device for optically detecting a defect.

According to one or more aspects of the present invention, external circular planar light is emitted to the dark field and thus is widely radiated in the transporting direction of the round wire rod so that light reflected from the surface can always reach the image sensor so that defect inspection can be performed irrespective of a change in the diameter or a vibration of the round wire rod. Therefore, when the device for detecting a surface defect of a round wire rod is used in a round wire manufacturing process, it is not required to adjust the device irrespective of changes in the diameter of the wire rod.

According to one or more aspects of the present invention, external light sources emitting circular planar light are used and are arranged such that circular beams of light therefrom overlap each other. The circular planar light sources can be easily arranged compared to linear light sources and the amount of the overlapping light beams increases when a wire rod having a small diameter. Even if the alignment of the image sensor or the alignment of the light beams emitted by the external light sources is minutely changed, the device for detecting a surface defect can be stably used.

According to one or more aspects of the present invention, the light sources can be selectively turned on or off when it is required to adjust the number of light sources according to the outer shape of a wire rod. The intensity of luminance can be adjusted remotely according to the average luminance on the surface of the wire rod. The state of the lighting device can be remotely diagnosed, and if lighting is not properly carried out, a warning signal can be automatically generated.

According to one or more aspects of the present invention, the guide is made of stainless steel and one end of the guide is tapered like a cone in order to minimize interference on a line along which external light is emitted.

According to one or more aspects of the present invention, the center wavelength of the optical filter is set in the range from 450 nm to 490 nm so as to remove the influence of spontaneous emission of a hot wire rod. Defect information on the surface of a wire rod can be correctly detected by allowing only reflection characteristics of blue light of externally-emitted light to enter the image sensor. Further, the optical filter can shield radiation heat generated from the hot wire rod to thereby prevent the temperature of the image sensor from rising.

According to one or more aspects of the present invention, an image having a predetermined definition can be acquired from an environment in which the transporting speed of a wire rod changes, and thus the length, width, size and defect location can be correctly acquired.

According to one or more aspects of the present invention, the image sensor and the emission angle of the external light source are arranged to produce a dark field, which reduces an influence of surface scales compared a bright field of the related art. Therefore, it is not required to install the device for detecting a defect of wire rods in a place right downstream of rolling.

According to one or more aspects of the present invention, the image sensor and the emission angle of the external light source are arranged to produce double dark fields, and particularly, arranged with respect to the transporting direction and the radial direction of a round wire rod to produce dark fields, respectively. This construction can sensitively detect changes in the edge inclination of a defect both in the transporting direction and in the radial direction of the round wire rod. Accordingly, the defect detection performance of the device for detecting a surface defect is significantly improved over that of the related art device for optically detecting a defect.

According to one or more aspects of the present invention, external circular planar light is emitted to the dark field and thus is widely radiated in the transporting direction of the round wire rod so that light reflected from the surface can always reach the image sensor so that defect inspection can be performed irrespective of a change in the diameter or a vibration of the round wire rod. Therefore, when the device for detecting a surface defect of a round wire rod is used in a round wire manufacturing process, it is not required to adjust the device irrespective of changes in the diameter of the wire rod.

According to one or more aspects of the present invention, the external light sources emitting circular planar light are used and are arranged such that circular beams of light therefrom overlap each other. The circular planar light sources can be easily arranged compared to linear light sources and the amount of the overlapping light beams increases when a wire rod having a small diameter. Even if the alignment of the image sensor or the alignment of the light beams emitted by the external light sources is minutely changed, the device for detecting a surface defect can be stably used.

According to one or more aspects of the present invention, the light sources can be selectively turned on or off when it is required to adjust the number of light sources according to the outer shape of a wire rod. The intensity of luminance can be adjusted remotely according to the average luminance on the surface of the wire rod. The state of the lighting device can be remotely diagnosed, and if lighting is not properly carried out, a warning signal can be automatically generated.

According to one or more aspects of the present invention, the guide is made of stainless steel and one end of the guide is tapered like a cone in order to minimize interference on a line along which external light is emitted.

According to one or more aspects of the present invention, the center wavelength of the optical filter is set in the range from 450 nm to 490 nm so as to remove the influence of spontaneous emission of a hot wire rod. Defect information on the surface of a wire rod can be correctly detected by allowing only reflection characteristics of blue light of externally-emitted light to enter the image sensor. Further, the optical filter can shield radiation heat generated from the hot wire rod to thereby prevent the temperature of the image sensor from rising.

MAJOR REFERENCE NUMERALS/SYMBOLS OF THE DRAWINGS

Figure 1:
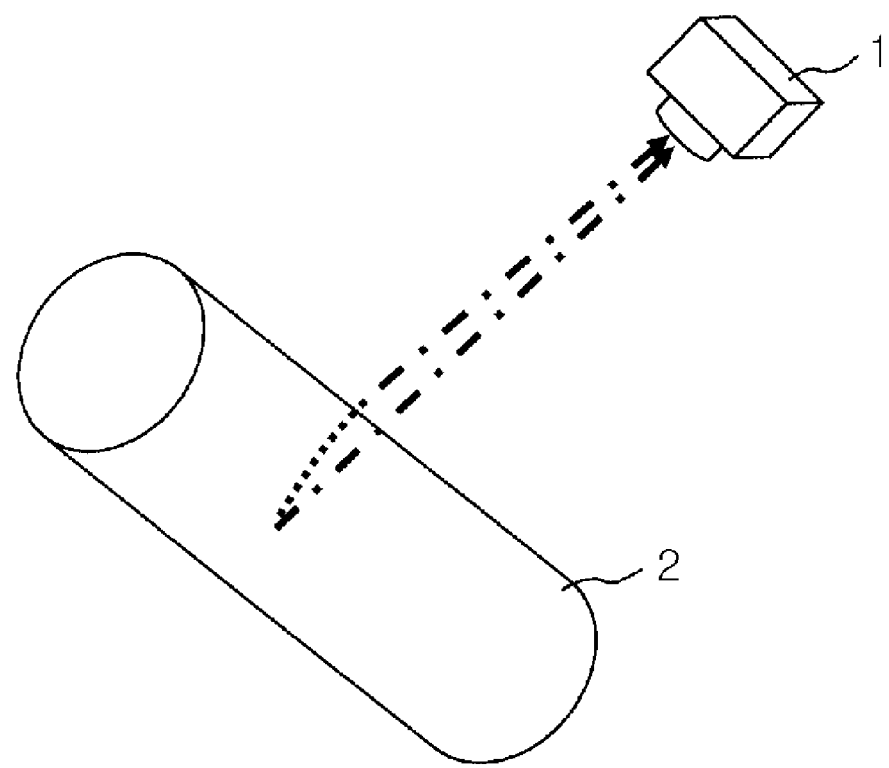
FIG. 1 is a perspective view illustrating a device for detecting a surface defect based on spontaneous emission of a hot round wire rod.

1: optical sensor
2: round wire rod
3, 12, 17, 20: lighting device
5: optical filter 6: slab
9: inspector
10: guides
11: signal-processing unit
13: optical sensor
14: optical lens
15: beam splitter
16: optical filter
18: speedometer
19: guides
22: luminance controller
23: server

DETAILED DESCRIPTION OF THE INVENTION

Exemplary embodiments of the present invention will now be described in detail with reference to the accompanying drawings. The present invention may, however, be embodied in many different forms and should not be construed as limited to the embodiments set forth herein. In the drawings, the same reference numerals are used to designate the same or similar components throughout.

There are two methods for detecting a defect of a round wire rod using light-reflecting characteristics as follows:

1. First Method

Figure 5:
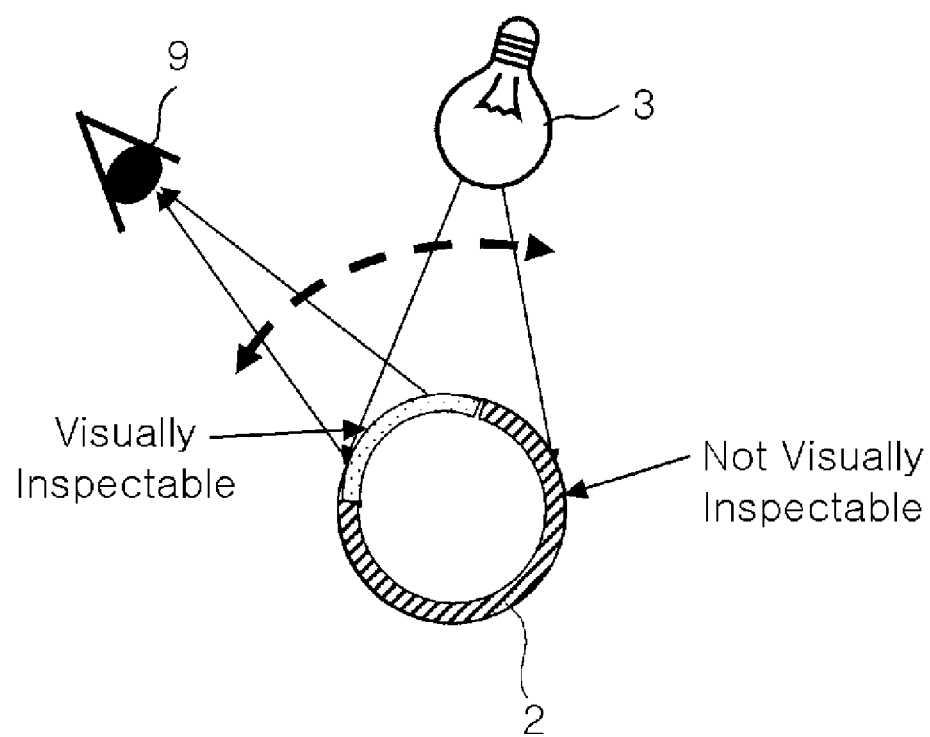
FIG. 5 is a view illustrating the state in which an inspector is performing a visual inspection on a defect of a hot round wire rod using a lighting device in a manufacturing process after the wire rod is rolled.

As shown in FIG. 5, in a process of manufacturing a wire rod 2, an inspector 9 can sample a predetermined portion of the round wire rod 2 and inspect the sampled portion using an external lighting device. In this case, it is difficult to inspect the entire length of the round wire rod 2, and in particular, only a limited portion of the surface of the round wire rod 2 can be inspected since the inspector 9 inspects the wire rod 2 with the eye. In addition, the round wire rod 2 cannot be inspected in detail since it is manufactured more quickly than the metal plated.

In general, a main object of performing a defect test in the process of manufacturing the wire rod 2 is to find a defect in an earlier stage of the manufacturing process and remove an error in the manufacturing process in order to prevent massive defects from occurring continuously.

With the method in which the inspector 9 visually inspects the completely-manufactured round wire rod 2, it is difficult to inspect the entire length of the wire rod 2 since the wire rod 2 is long and wound. It is also difficult to inspect the inside of a coil of the wound wire rod 2 with the eye. Although the object of detecting a defect of the completely-manufactured round wire rod 2 is to deliver a product, which does not contain a defect, to a customer, a product having a defect may be delivered to the customer since it is impossible to inspect the entire surface and length of the completely-manufactured round wire rod 2.

Below, a description will be given of the detection method in which an external lighting device 3 emits light to the outer surface of the round wire rod 2, an optical sensor receives reflected light from the surface of the round wire rod 2, and an image signal based on the received reflection light is analyzed to find a defect.

Figure 6:
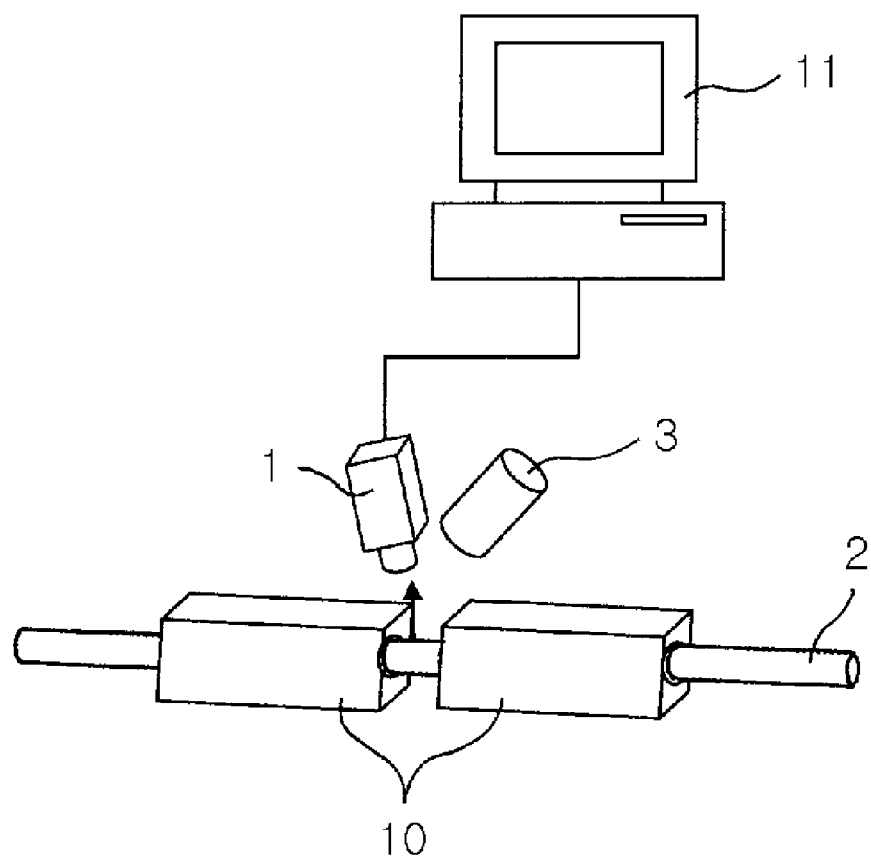
FIG. 6 is a schematic view illustrating a conventional device for detecting a surface defect of a hot round wire rod.

Referring to FIG. 6, the method of finding a defect by analyzing an image signal requires an external lighting device 3, an optical sensor 1 for receiving light reflected from the surface of the round wire rod 2 and a signal-processing unit 11 for analyzing an electric signal received from the optical sensor in order to find a defect. The method also requires guides 10 for restricting a transportation path of the round wire rod 2.

The method for detecting a defect using the lighting device 3, the optical sensor and the signal-processing unit 11 is well-known in the art. Some patents involve the lighting device 3 and the signal-processing unit 11 in order to improve the efficiency of detecting a defect. Below, a description will be given of the disclosure of such patents.

U.S. Pat. No. 6,859,285 discloses a method applicable to an environment in which light having 650 nm wavelength and light having surrounding wavelength are emitted simultaneously. The method involves emitting external light to a test object, the external light having a wavelength different from that of light emitted from an external hot material. Then, the optical sensor receives both reflection light of the external light and light emitted from the hot material, and amplifies the intensity of the external light in order to increase the influence of the reflection light of the external light while decreasing the influence of the emission light from the hot material.

Figure 2:
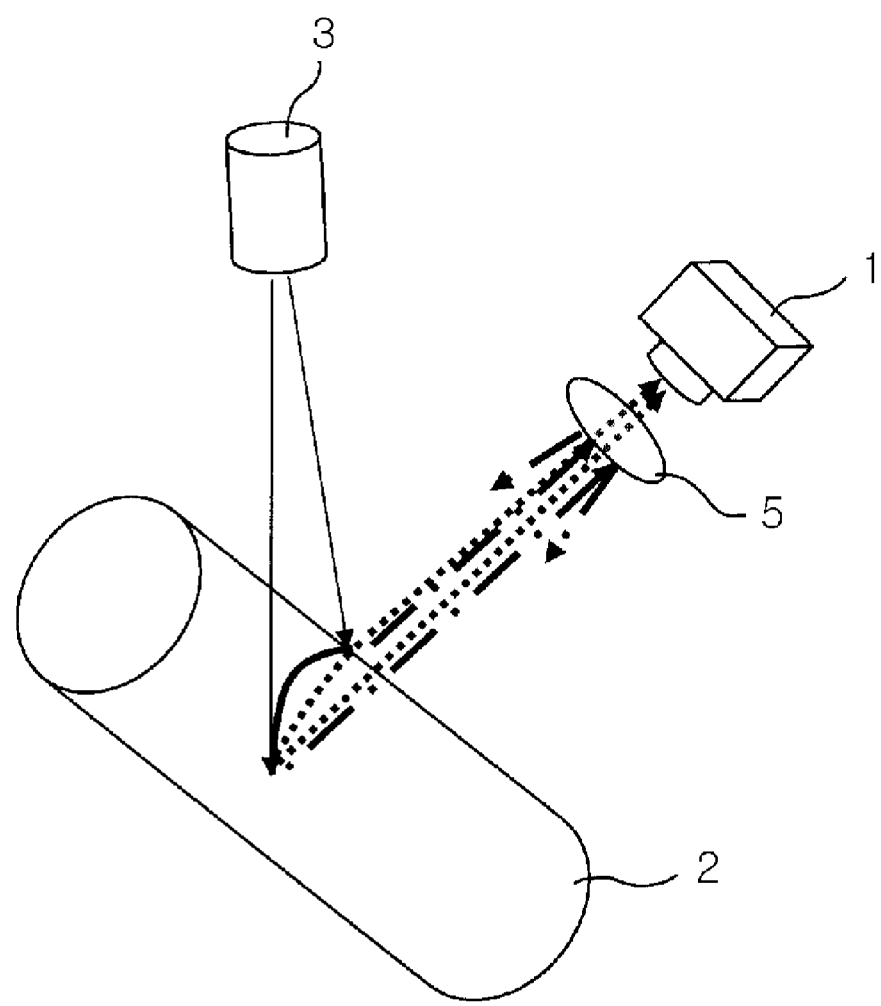
FIG. 2 is a perspective view illustrating a device for detecting a surface defect of a hot round wire rod by emitting external light to the wire rod and using light reflected from the wire rod.
Figure 3:
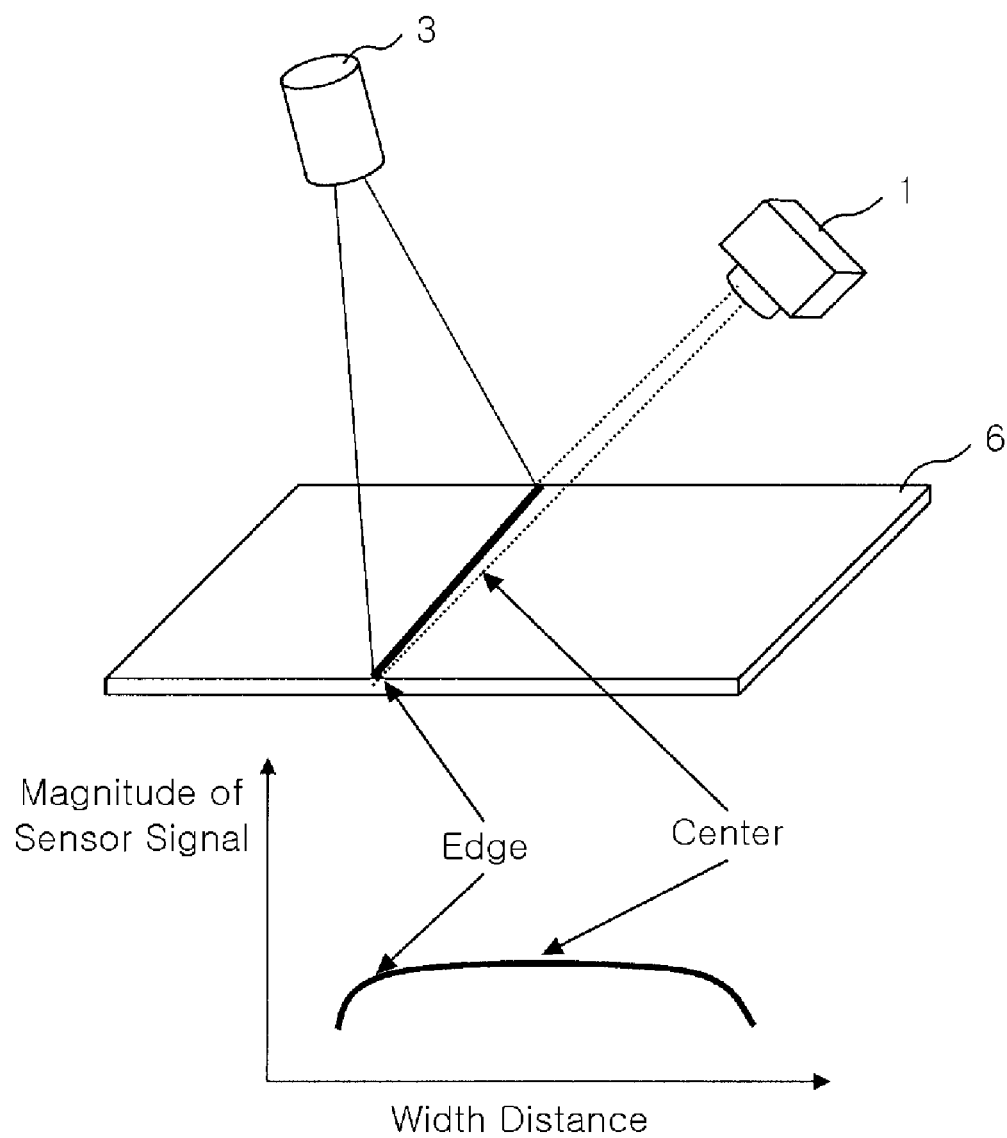
FIG. 3 is a graph illustrating the size of a signal from a signal detection sensor according to a width direction in a device for detecting a surface defect of a steel slab.
Figure 4:
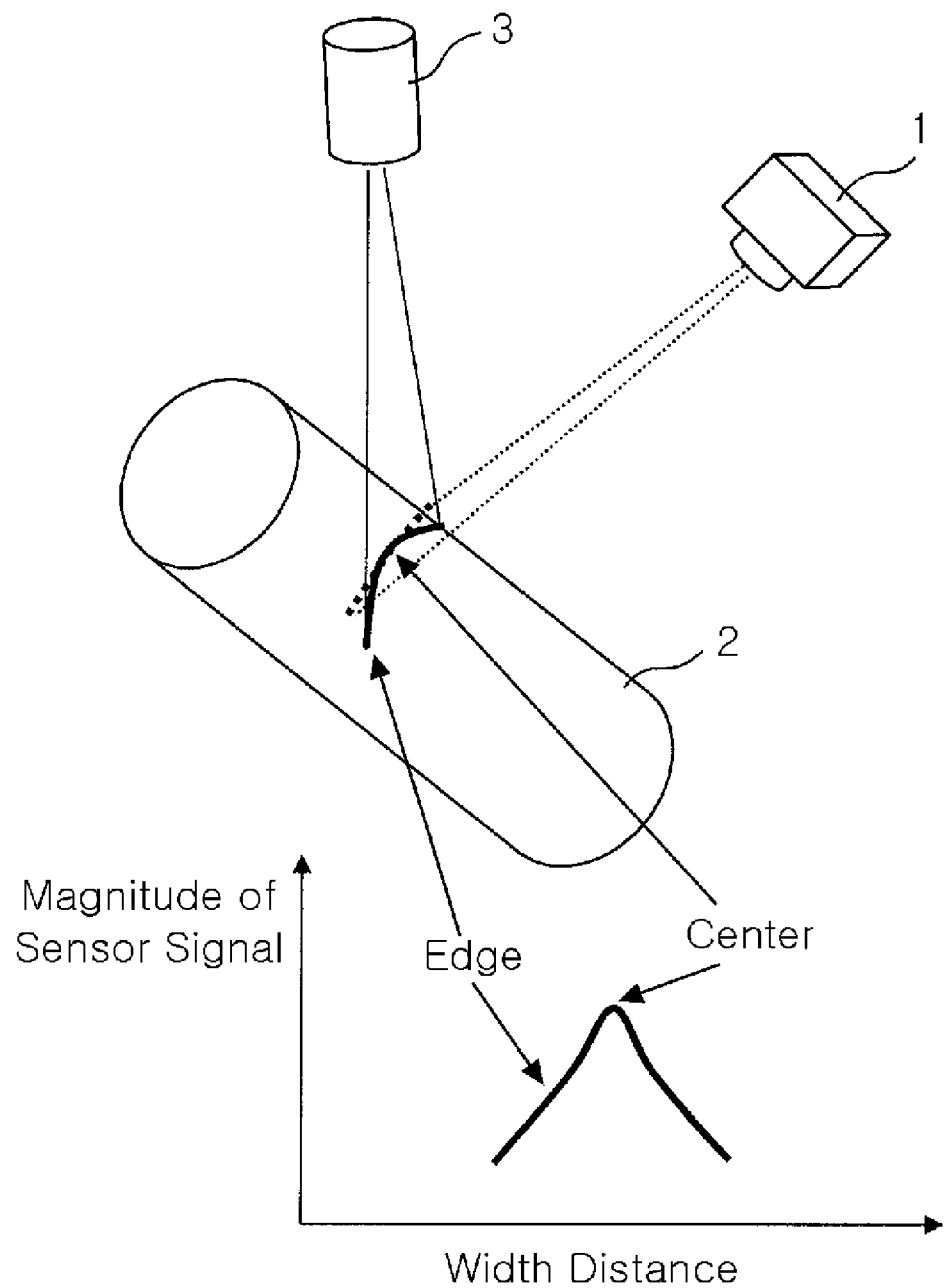
FIG. 4 is a graph illustrating the size of a signal from a signal detection sensor according to width direction in a device for detecting a surface detect of a round steel rod.

U.S. Pat. No. 6,859,285 used external light (i.e., a halite lamp: 435 nm, 550 nm, 575 nm) discriminated from emission light of a hot round wire rod. As shown in FIG. 2, an optical filter 5 transmitting only a predetermined wavelength band is installed in the leading end of the optical sensor 1 in order to remove the influence of the emission light from the hot round wire rod 2.

Figure 7:
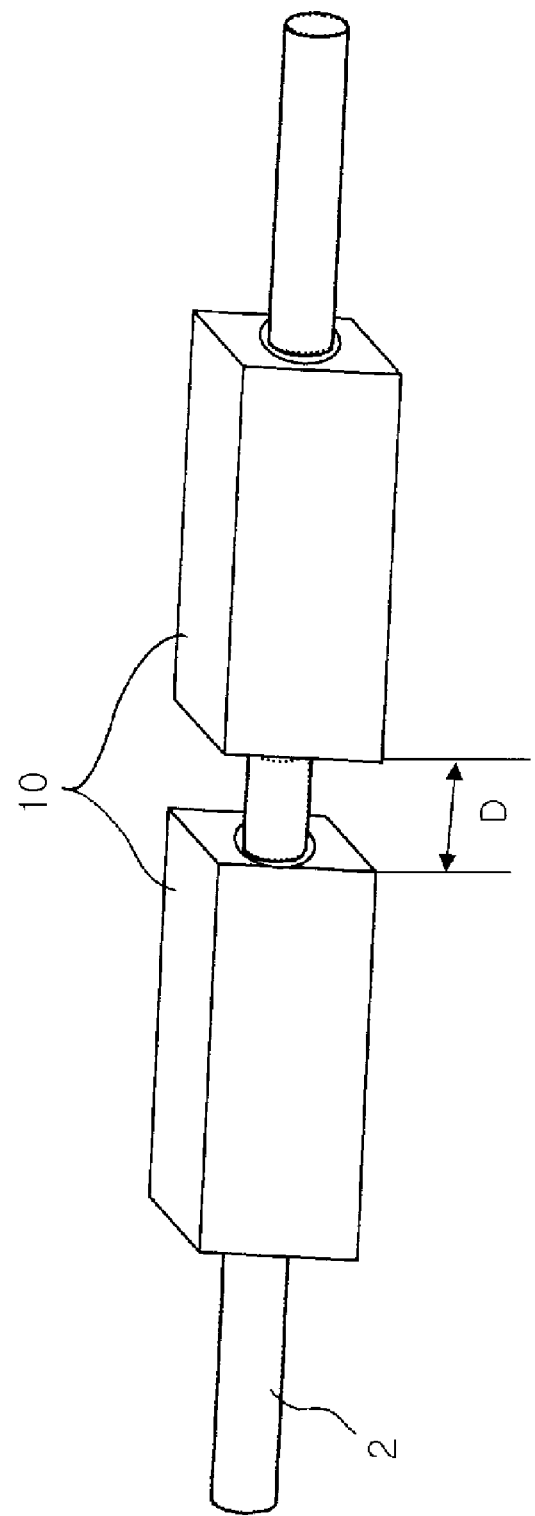
FIG. 7 is an enlarged view of the guides shown in FIG. 6.

U.S. Pat. No. 6,950,546 proposes a system for optically detecting a surface defect. This system is suitable for the case in which the guides 10 as shown in FIG. 7 are used to restrict the predefined transportation path of the hot round wire rod 2, which is being transported at a high speed. The distance D between the guides 10 for restricting the path of the round wire rod 2, which is being transported at a high speed, cannot exceed a maximum value 50 mm. An optical sensor, a lighting device and a signal-processing unit were devised to inspect a surface defect of the round wire rod 2 in these circumstances.

Figure 8:
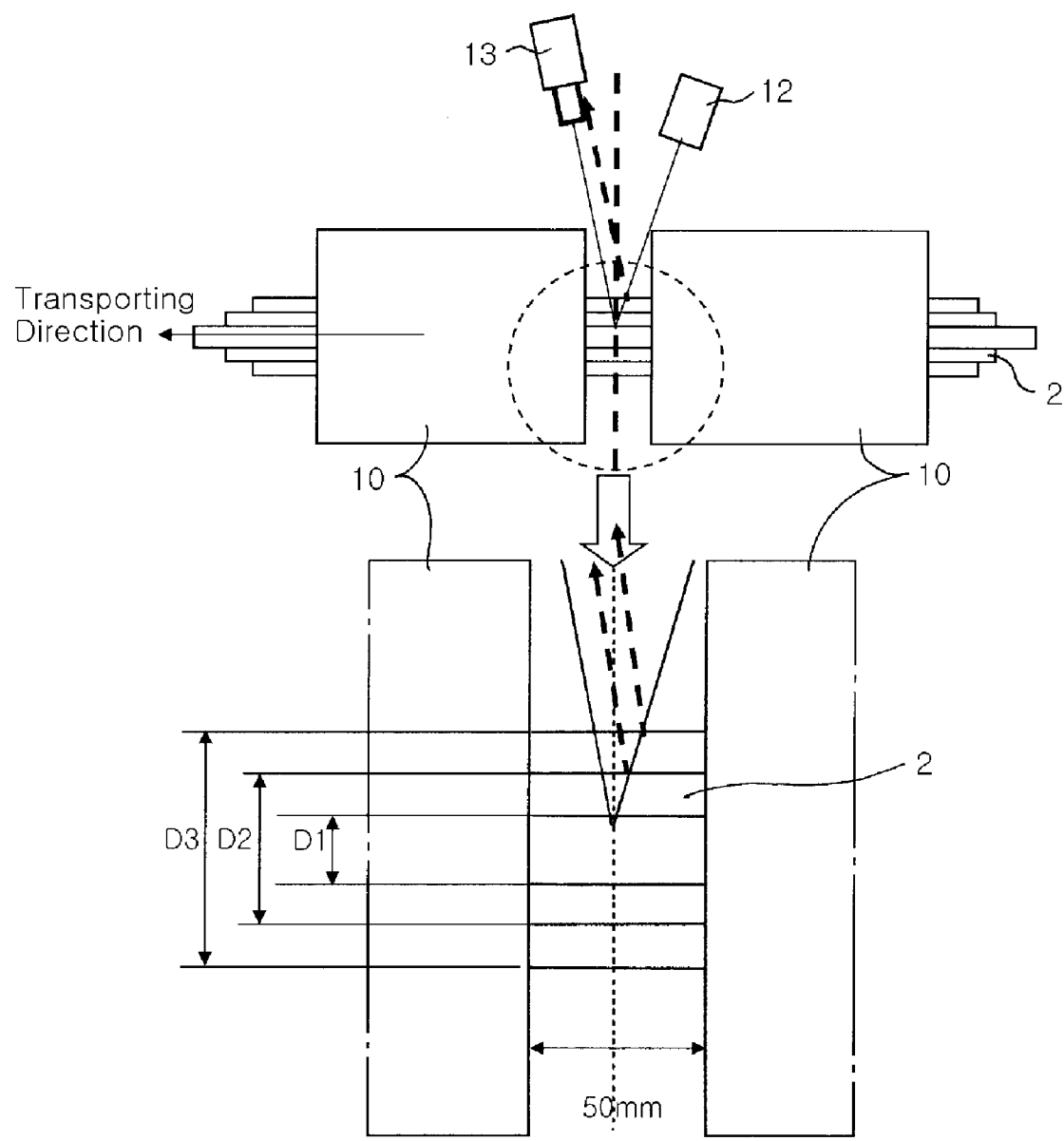
FIG. 8 is a view illustrating a change in a path of reflection light in response to a change in the diameter of a round wire rod or vibration in the case where a conventional device for detecting a surface defect of hot round wire rods.

When the lighting device 12 emitting linear light as shown in FIG. 8 is used, a reflecting position of the linear external light will be changed by a vibration of the wire rod 2 or a variation in the diameter of the wire rod 2, the path of which is restricted by the guides 10. Then, characteristics of signals detected by an optical sensor 13 will not be constant.

Figure 9:
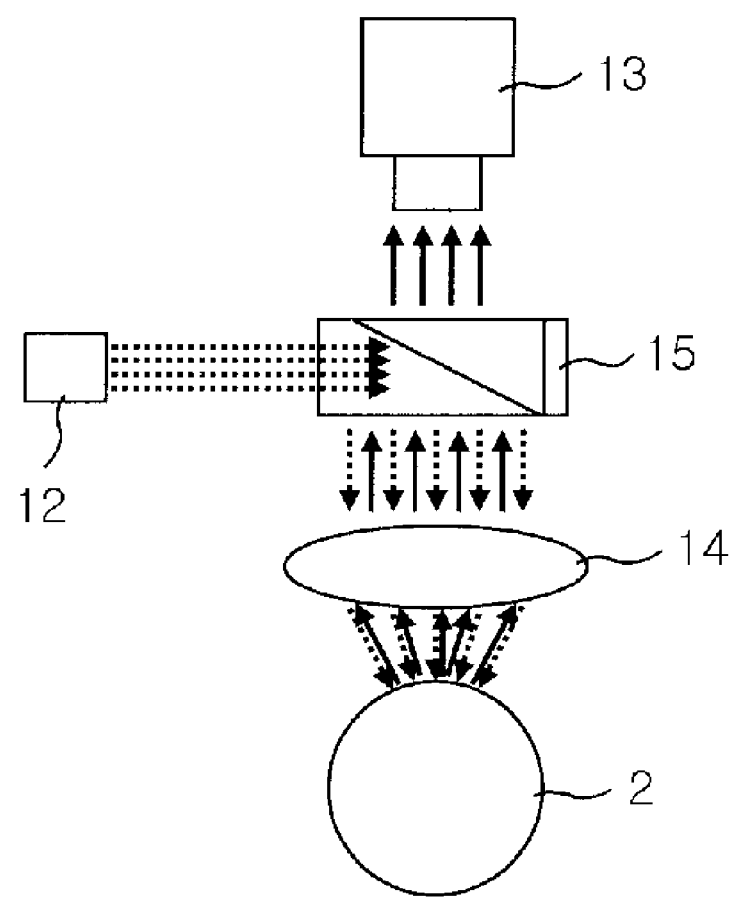
FIG. 9 is a view illustrating a path of light emitted to a bright field using a beam splitter in order to detect a surface defect of a hot round wire rod.

As shown in FIG. 9, when the lighting device 12 emitting linear light is used, it is required to make the path of emission light be identical with the path of reflecting light using a beam splitter 15. However, this is physically difficult. When the beam splitter 15 is used, 50% of light emitted from the lighting device 12 passes through the beam splitter 15 to reach the round wire rod 2 through an optical lens 14. When the light is reflected from the round wire rod 2 on the assumption that the round wire rod 2 perfectly reflects the light, the reflected light passes through again the optical lens 14, and the beam splitter 15 transmits 25% of the original light to reach the optical sensor 13. Accordingly, the intensity of a light source has to be increased four times in general reflection conditions.

In U.S. Pat. No. 6,950,546, the angle between the optical sensor and the external lighting device is set 1° in order to exclude the beam splitter. Even in this case, if a small width of external linear lighting is provided, reflected light of external light cannot reach the optical sensor 13 when a change in the diameter of the round wire rod 2 or the amplitude of vibration of the round wire rod 2 is relatively large.

Figure 11:
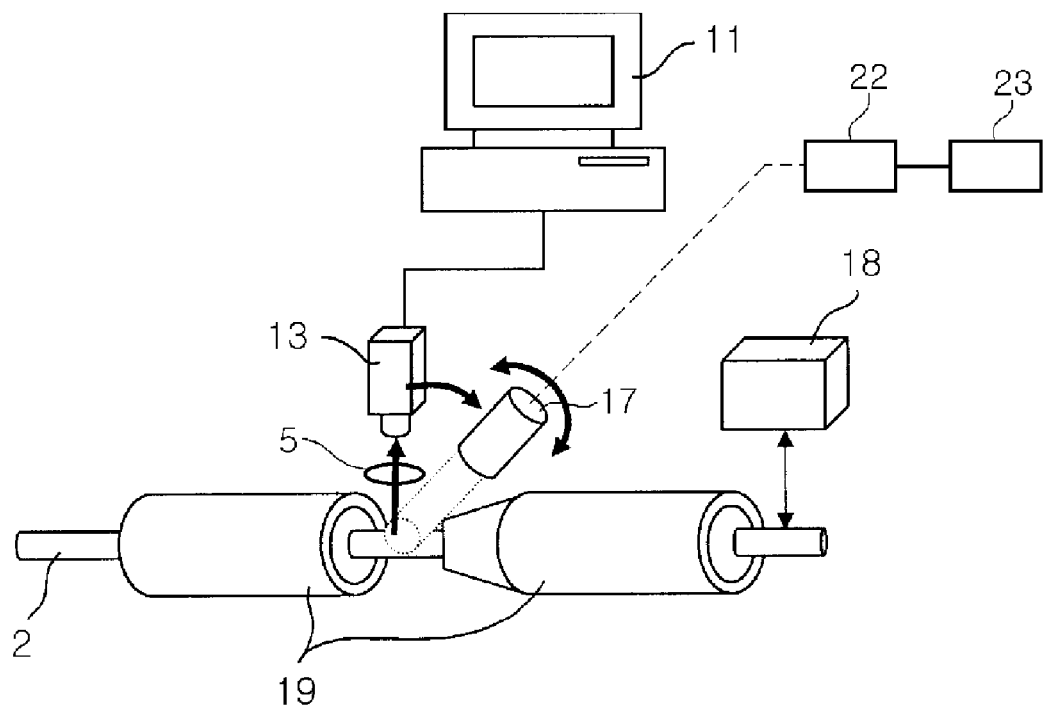
FIG. 11 is a view illustrating a change in the angle between a lighting device and an optical sensor in the device for detecting a surface defect of a round steel rod according to the present invention.

When compared to U.S. Pat. No. 6,950,546, which disclosed the device for detecting a surface defect of a hot round wire rod using a conventional optical sensor, the present invention has following characteristics:

(1) Regarding system construction: U.S. Pat. No. 6,950,546 includes the optical sensor 1, the linear lighting device 3, the signal-processing unit 11 and the guides 10 shaped as a rectangular column. Referring to FIG. 11, the present invention includes a lighting device 17, an optical sensor 13, a signal-processing unit 11, a speedometer 18, guides 19, an optical filter 5, a luminance controller 22 and a server 23. The lighting device 17 acts as a surface light source to emit circular light, the optical sensor 13 receives the light of the lighting device 17 reflected from the round wire rod 2, which is being transported, generates an optical signal from the reflecting light, and converts the optical signal into an image signal. The signal-processing unit 11 receives the image signal from the optical sensor 13 and acquires surface information of the round wire rod 2 from the image signal. The speedometer 18 detects the moving speed of the round wire rod 2, and the guides 19 restrict the path of the round wire rod 2. The optical filter 5 is provided under the optical sensor 13 to receive the light reflected from the round wire rod 2. The optical filter 5 transmits a blue wavelength band to be sent to the optical sensor but does not transmit an infrared wavelength band. The luminance controller 22 detects a current supplied to the lighting device 17 and monitors the light emitted by the current. The server 23 turns on or off the luminance controller 22 or controls the operation of the luminance controller 22 via Transmission Control Protocol/Internet Protocol (TCP/IP).

In the above-described construction, the speedometer 18 can be implemented with a laser speedometer. The guides 19 are made of stainless steel, and are shaped as a circular column to surround the round wire rod 2. One end of the guide 19 is conically shaped. In the case where a plurality of the lighting devices 17 are provided, the server 23 selectively turns on or off the lighting devices 17. The server 23 produces a warning sound when detecting that the lighting device 17 does not have a predetermined level of luminance.

According to the above-described construction, even if the transporting speed is changed according to a change in the diameter of the hot round wire rod 2 to be tested, the speedometer detects the round wire rod 2 whenever the wire rod 2 is transported by a predetermined length. In this fashion, surface information of the round wire rod 2 can be thoroughly acquired and the size reference of a defection test can be set constantly irrespective of the change in the diameter of the round wire rod 2.

Figure 10:
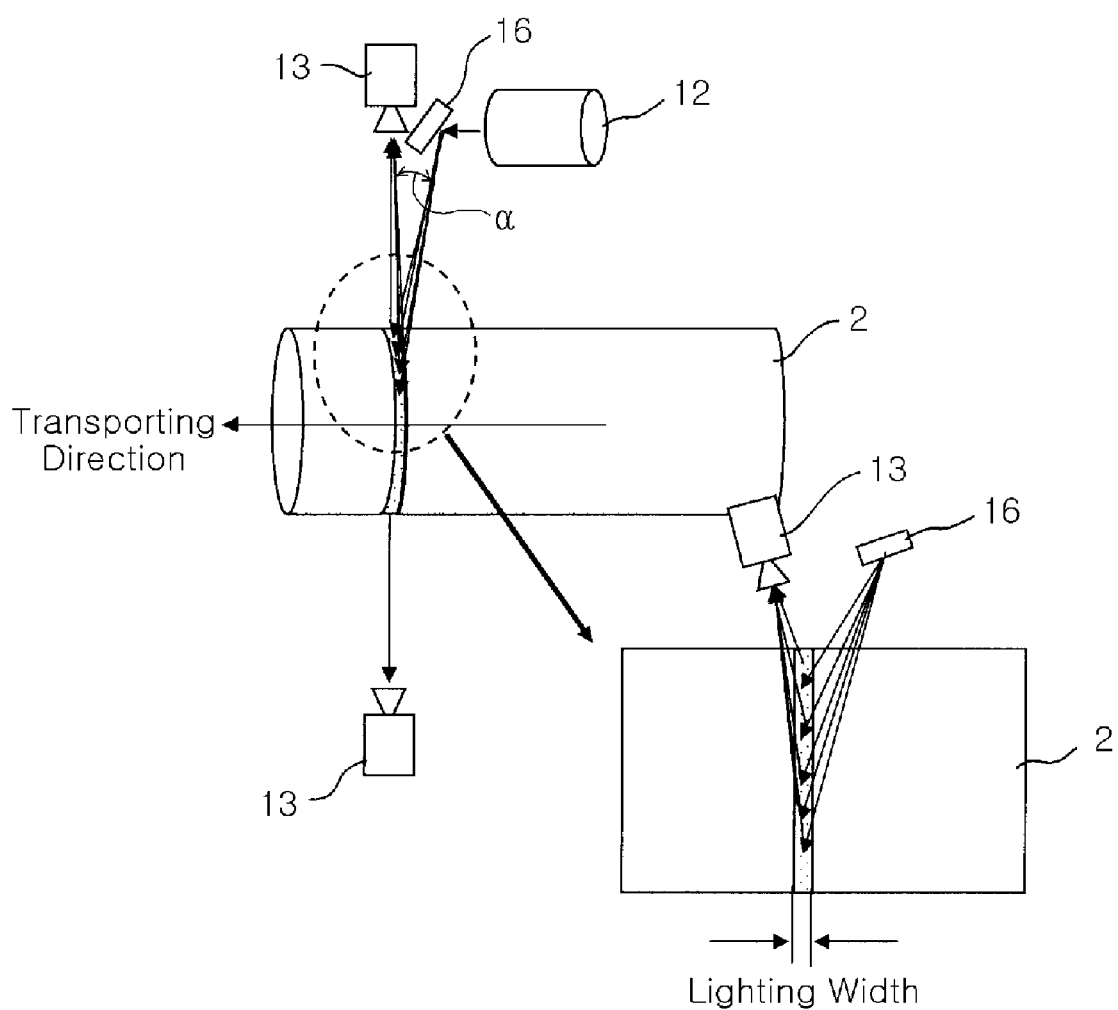
FIG. 10 is a view illustrating the state in which linear light is emitted and reflection light enters an optical sensor in a conventional device for detecting a surface defect of hot round wire rods.

(2) Regarding arrangement of optical sensor: As shown in FIG. 10, the optical sensor 13 is arranged in a bright field directed substantially perpendicular to the transporting direction of the round wire rod 2. When light emitted from the lighting device 12 is reflected as an optical signal from the round wire rod 2, the optical sensor 13 receives the optical signal and acquires an image from the received signal. An optical filter 16 is provided between the lighting device 12 and the optical sensor 13. According to the present invention, however, the direction in which the optical sensor receives light reflected from the round wire rod is angled in the range from 50° to 90° with respect to the transporting direction of the round wire rod, and the direction of light emitted by the lighting device is angled in the range from 45° to 65° with respect to the transporting direction of the round wire rod. In addition, the direction of light emitted by the lighting device is angled in the range from 45° to 60° with respect to the vertical radial direction of the wire round rod.

According to U.S. Pat. No. 6,950,546, since the bright field is defined by the emission angle of the optical sensor and the external lighting device, the installation position of the device for detecting a surface defect of a round wire rod is restricted to a place where oxidation scales do not occur on the surface right after rolling or injection of common steel. When the defect-detecting device of the present invention is distanced from the rolling or injection position, oxygen in the air may chemically react with carbon or components of hot steel, thereby forming a thin scale layer on the surface of hot steel. Since the surface roughness of scales is generally smaller than that of rolled steel rod so as to change the reflectivity of light, it is difficult to discriminate a scale from a defect.

In the present invention, the angle between the optical sensor and the external lighting device and the emission angle of the external lighting device can be adjusted as shown in FIG. 11. With this arrangement, even if a scale layer is formed on the surface of hot steel, an acquired image is rarely influenced by scales.

In U.S. Pat. No. 6,950,546, the position of the defect-detecting device is limited to a time point before the scales are formed right after rolling of steel. According to the present invention, however, the angle of the optical sensor is changed so that scale characteristics do not appear from an image even after the scales are formed. Advantageously, the range of arrangement of the defect-detecting device can be increased.

Figure 12:
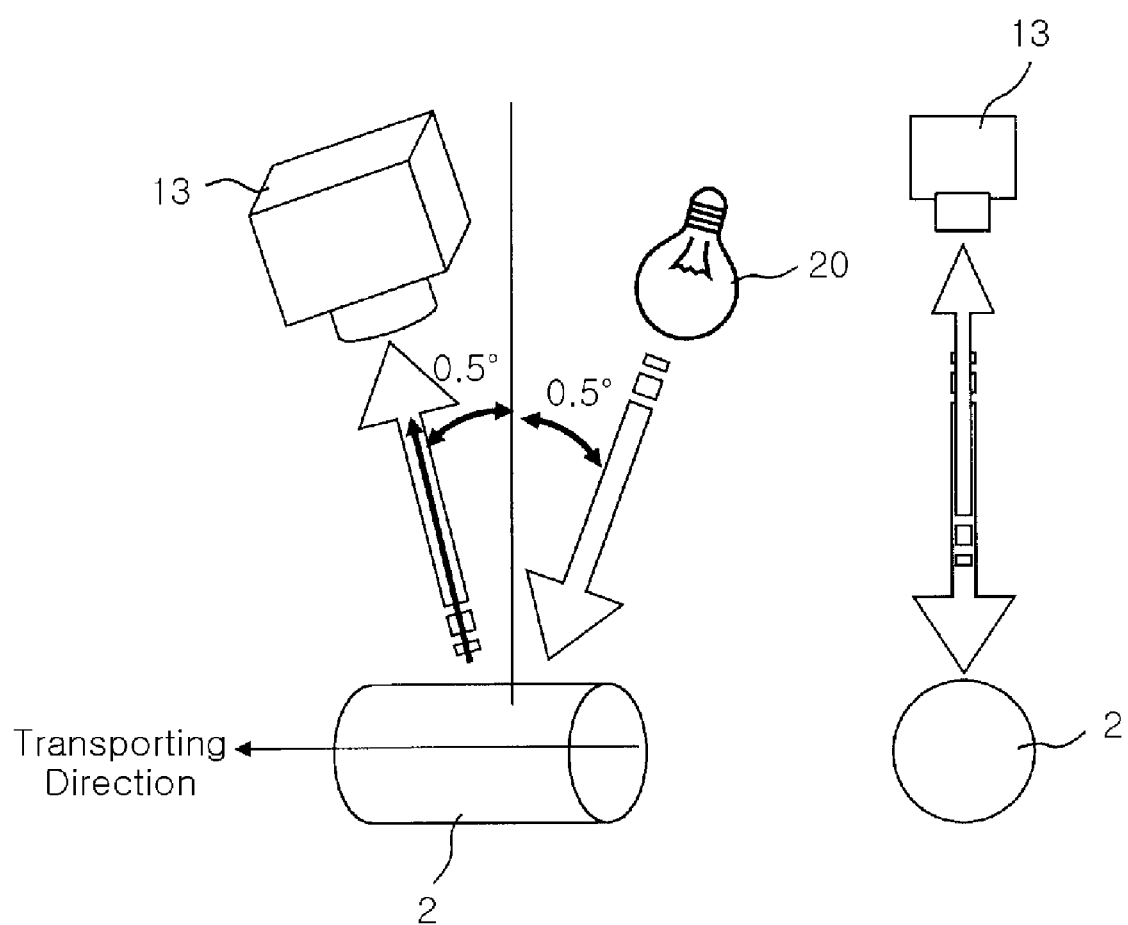
FIG. 12 is a view illustrating a change in the angle between the lighting device and the optical sensor in the device for detecting a surface defect of a round steel rod according to the related art.

(3) Regarding arrangement of lighting device that externally emits light: As shown in FIG. 12, U.S. Pat. No. 6,950,546 uses the external lighting device 20, which emits light in a direction inclined 0.5° with respect to a perpendicular of the transporting direction of the round wire rod 2 and inclined 0.5° with respect to the vertical radial direction of the round wire rod 2. In this arrangement of the lighting device, when an edge of a defect is close to the vertical radial direction of the round wire rod 2, the ratio of signal to noise (S/N) caused by a defect (see FIG. 13) is small.

Figure 14:
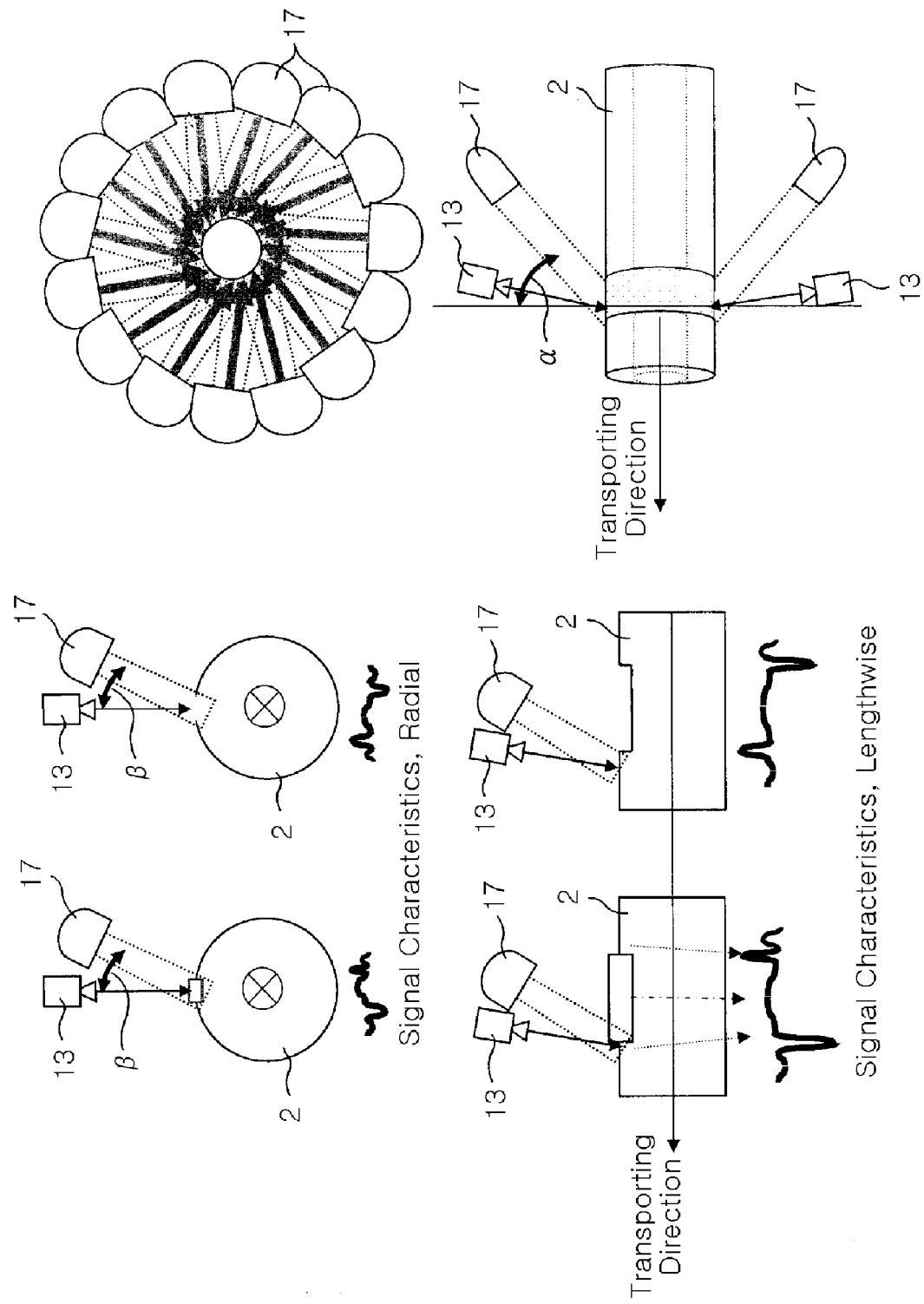
FIG. 14 is a view illustrating radial signal characteristics and lengthwise signal characteristics according to arrangement of the lighting device and the optical sensor in the device for detecting a surface defect of a round steel rod according to the present invention.

As shown in FIG. 14, in the present invention, the external lighting device 17 emits light in a direction inclined at a relatively large angle with respect to a perpendicular of the transporting direction of the round wire rod 2 and inclined at a predetermined angle with respect to the vertical radial direction of the round wire rod 2 (see dark fields). As in the present invention, when the light-emitting device is inclined with respect to both the perpendicular of the transporting direction and the vertical radial direction of the round wire rod 2, the ratio of signal to noise of a defect significantly increases as shown in the graph.

Figure 15:
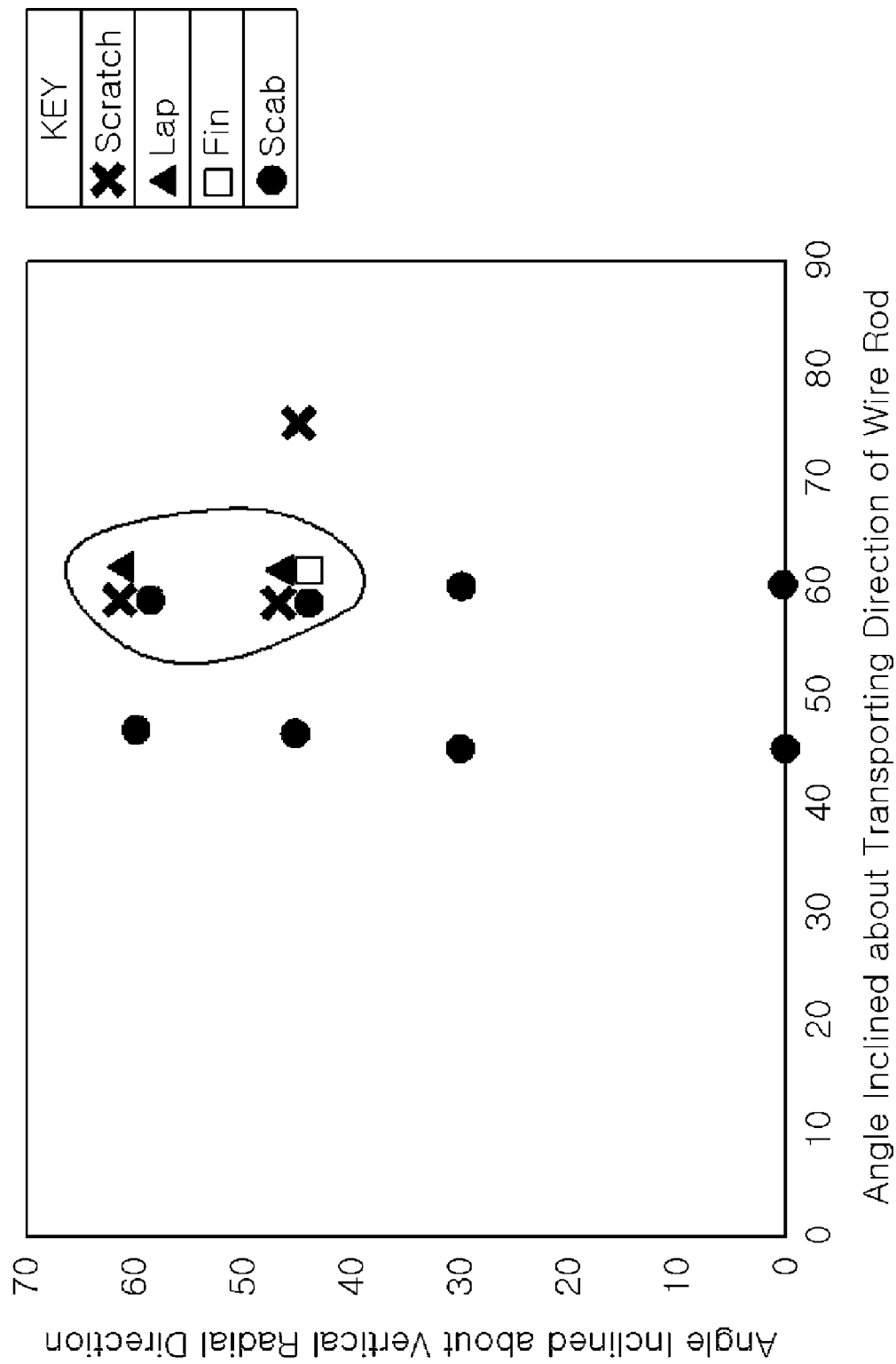
FIG. 15 is a graph illustrating surface defects of round wire rods according to angles inclined about the vertical radial direction and about the transporting direction of the wire rods.

Referring to FIG. 15, a description will be made of the ratios of signal to noise of surface defects according to changes in the angle inclined with respect to the transporting direction of a round wire rod and changes in the angle inclined with respect to the vertical radial direction of the round wire rod. Here, the surface defects of the round wire rod include scratch, lap, fin and scab. The maximum ratio of signal to noise is observed when light is emitted at an inclination in the range from 45° to 65° with respect to the perpendicular of the transporting direction of the wire rod and when light is emitted at an inclination in the range from 45° to 65° with respect to the vertical radial direction of the round wire rod.

Figure 16:
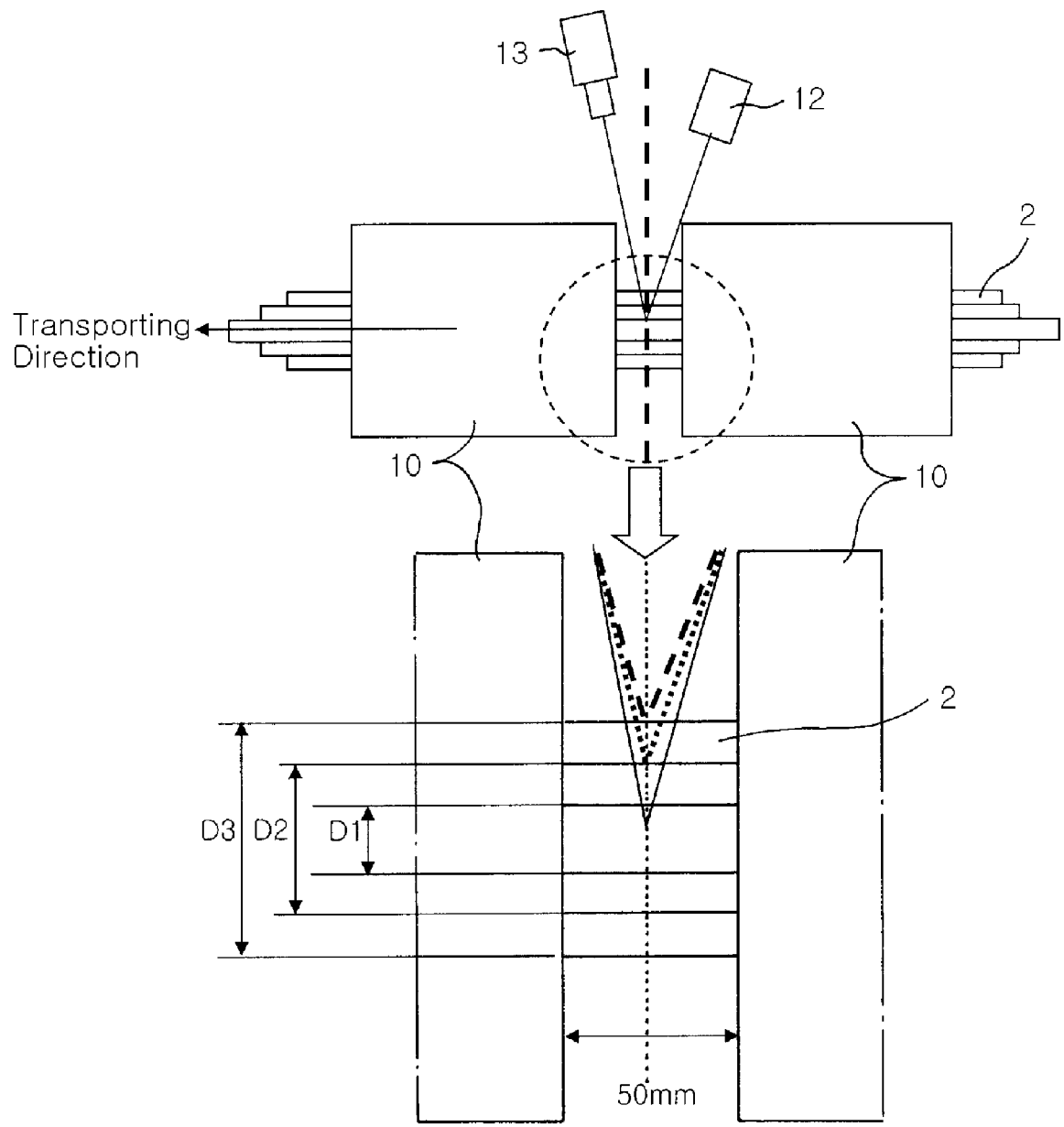
FIG. 16 is a view illustrating changes in the path of reflected light in response to changes in the diameter or vibrations of round wire rods in the case where the device for detecting a surface defect according to the related art is used.

(4) Regarding change in diameter of round wire rod: As shown in FIG. 16, U.S. Pat. No. 6,950,546 uses the external linear lighting device 12 and the optical sensor 13 that acquires linear image information. When the round wire rod 2 has a diameter D1, the angle of emitting light and the angle of the optical sensor 13 have to be aligned with solid lines, respectively. When the round wire rod 2 has a diameter D2, the angle of emitting light and the angle of the optical sensor 13 are adjusted to thin dotted lines, respectively. When the round wire rod 2 has a diameter D3, the angle of emitting light and the angle of the optical sensor 13 are adjusted to thick dotted lines, respectively.

Figure 17:
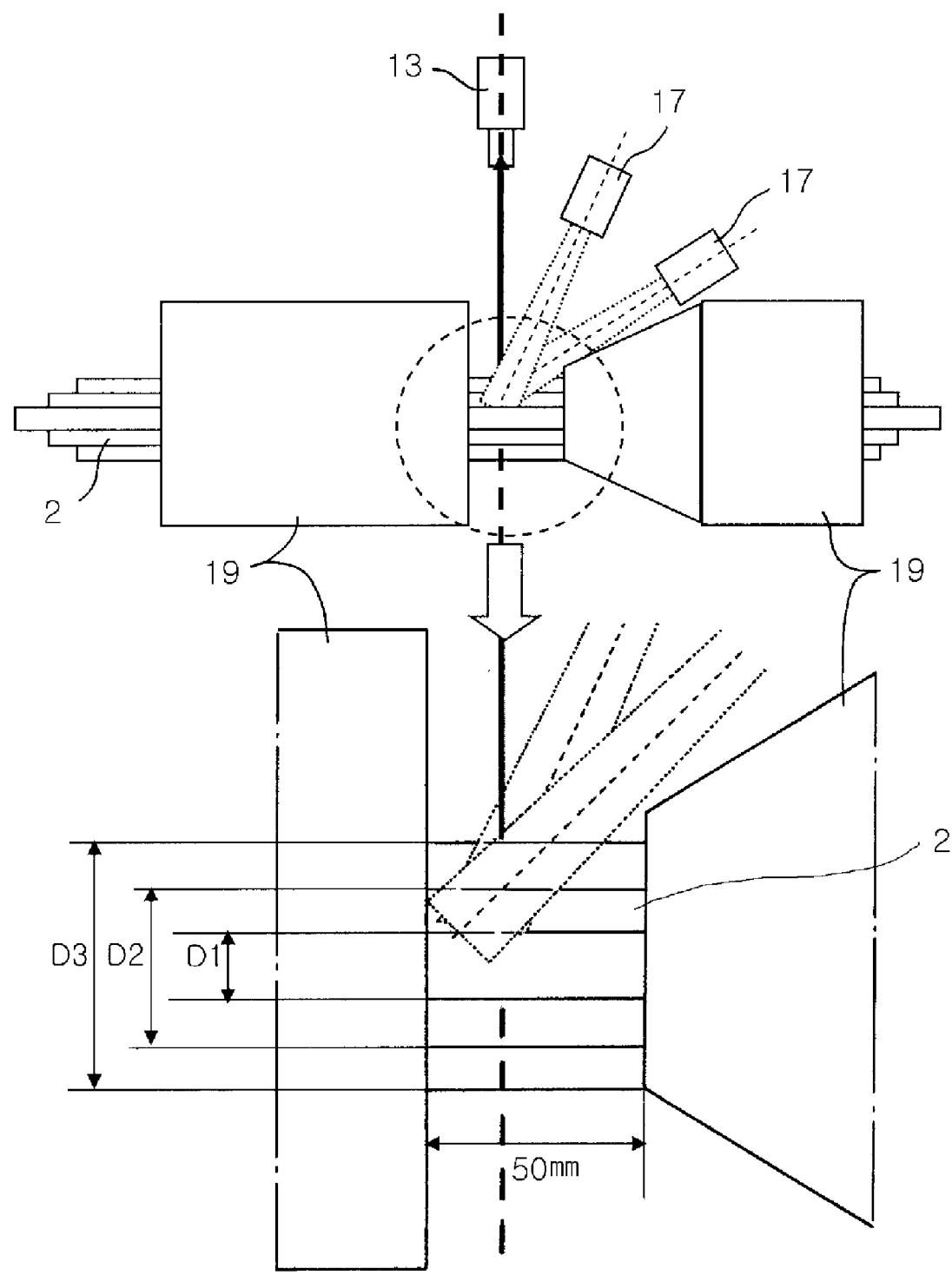
FIG. 17 is a view illustrating changes in the path of reflected light in response to changes in the diameter or vibrations of round wire rods in the case where the device for detecting a surface defect according to the present invention emits circular light to a dark field.

As shown in FIG. 17, the present invention used circular external light sources having high energy so that light emitted from the external lighting device 17 can be reflected to the optical sensor 13 even if the reflection point of the emitted light is changed when there is a change in the diameter of the round wire rod 2 or the round wire rod 2 vibrates in a vertical direction. Accordingly, when the circular external light of the present invention is used, the optical sensor 13 can detect light reflected from the surface of the round wire rod 2 so that a defect inspection can be stably performed even if there is a change in the diameter of the round wire rod 2 or the round wire rod 2 vibrates.

Figure 18:
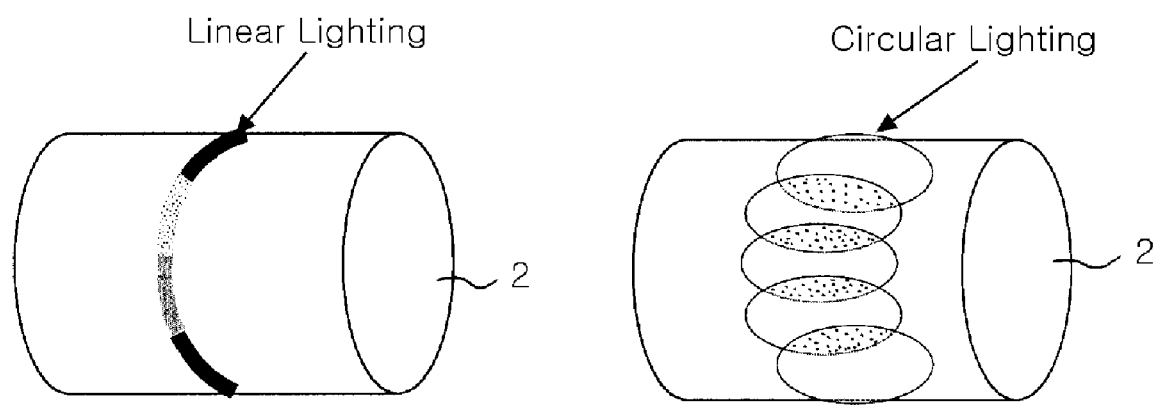
FIG. 18 is a view illustrating the state in which light beams are aligned on the round wire rod using the device for detecting a surface defect according to the related art and the device for detecting a surface defect according to the present invention.

(5) Regarding arrangement after external light is emitted to surface of round wire rod: According to U.S. Pat. No. 6,950,546, as shown in FIG. 18(*a*), it is difficult to linearly align external light on the surface of the round wire rod 2 or to linearly align the optical sensor to a surface point from which light is reflected since linear light is emitted to the surface of the round wire rod. In particular, when the defect-detecting device is deformed by an external impact, the angle of linearly emitting external light and the detection angle of the optical sensor can be changed precisely. This makes it impossible to properly perform an inspection.

In particular, U.S. Pat. No. 6,950,546 requires arranging the lighting device so as to emit external light at an angle 0.5° with respect to a perpendicular of the transporting direction of the round wire rod 2 and the optical sensor at an angle 0.5° with respect to the perpendicular of the transporting direction of the round wire rod 2 so as to receive reflected light. Accordingly, an inspection should be performed very precisely.

In the present invention, as shown in FIG. 18(*b*), circular planar light is emitted to the surface of the round wire rod 2. In particular, circular planar beams are made to overlap each other so as to form elliptical reflecting areas on the surface of the round wire rod 2. Accordingly, the lighting device and the optical sensor can be easily arranged. In addition, precise adjustment in the emission angle of the lighting device is not required since the circular planar light is emitted. Further, reliable defect tests can be ensured irrespective of a precise deformation in the detecting device caused by an external impact. In particular, even if the reflecting point of the external light on the round wire rod 2 is changed along or vertically with respect to the transporting direction of the round wire rod 2, the reflected light can positively reach the optical sensor owing to the circular planar light that lights a wider surface than the linear light of FIG. 18(*a*).

(6) Regarding luminance control, the present invention used, as the optical filter 5, a high power semiconductor device such as a light emitting diode having a center wavelength in the range from 450 nm to 490 nm. Further, a current supplied to the lighting device 17 was detected to independently control the intensity of luminance.

(7) Regarding guides for restricting transporting path of round wire rod manufactured at high speed: In U.S. Pat. No. 6,950,546, as shown in FIG. 7, the guides 10 for restricting the transportation path of the round wire rod 2 are shaped as a quadrangular column, so that the arrangement angle of the optical sensor and the external lighting device is very restricted.

In the present invention, as shown in FIG. 11, the cylindrical guides 19 are provided to increase the arrangement angle of the optical sensor 13 and the lighting device 17 for emitting external light. One end of the guide 19 is conically shaped.

(8) Regarding inspection performance according to angle of optical sensor and lighting device: Performance evaluation standards for optical defect inspection generally use a difference in level between signals detected by the optical sensor. Particularly, a difference in level between a signal detected from a normal surface and a signal detected from a defective surface is used.

Figure 13:
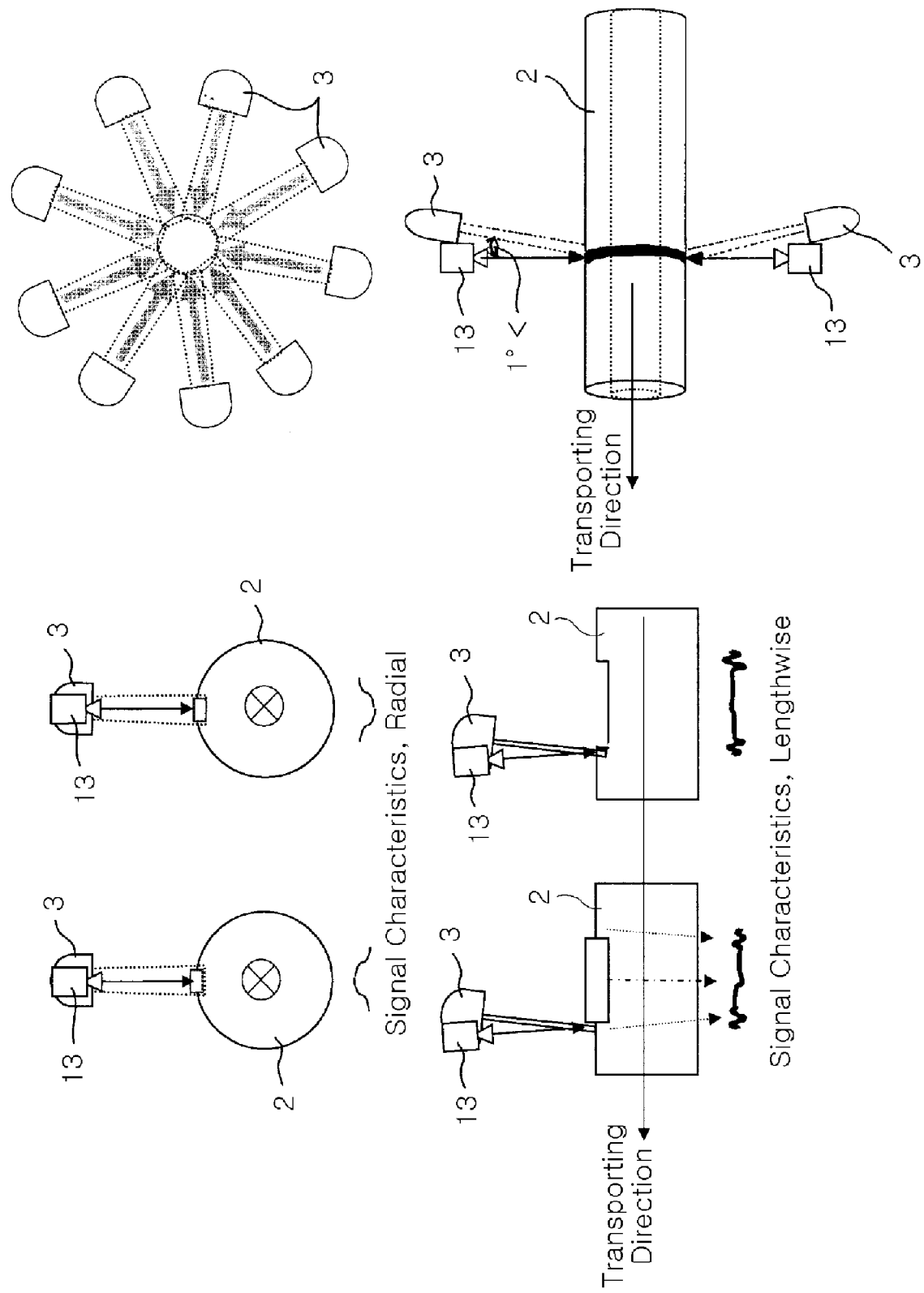
FIG. 13 is a view illustrating radial signal characteristics and lengthwise signal characteristics according to arrangement of the lighting device and the optical sensor in the device for detecting a surface defect of a round steel rod according to the related art.
Figure 19:
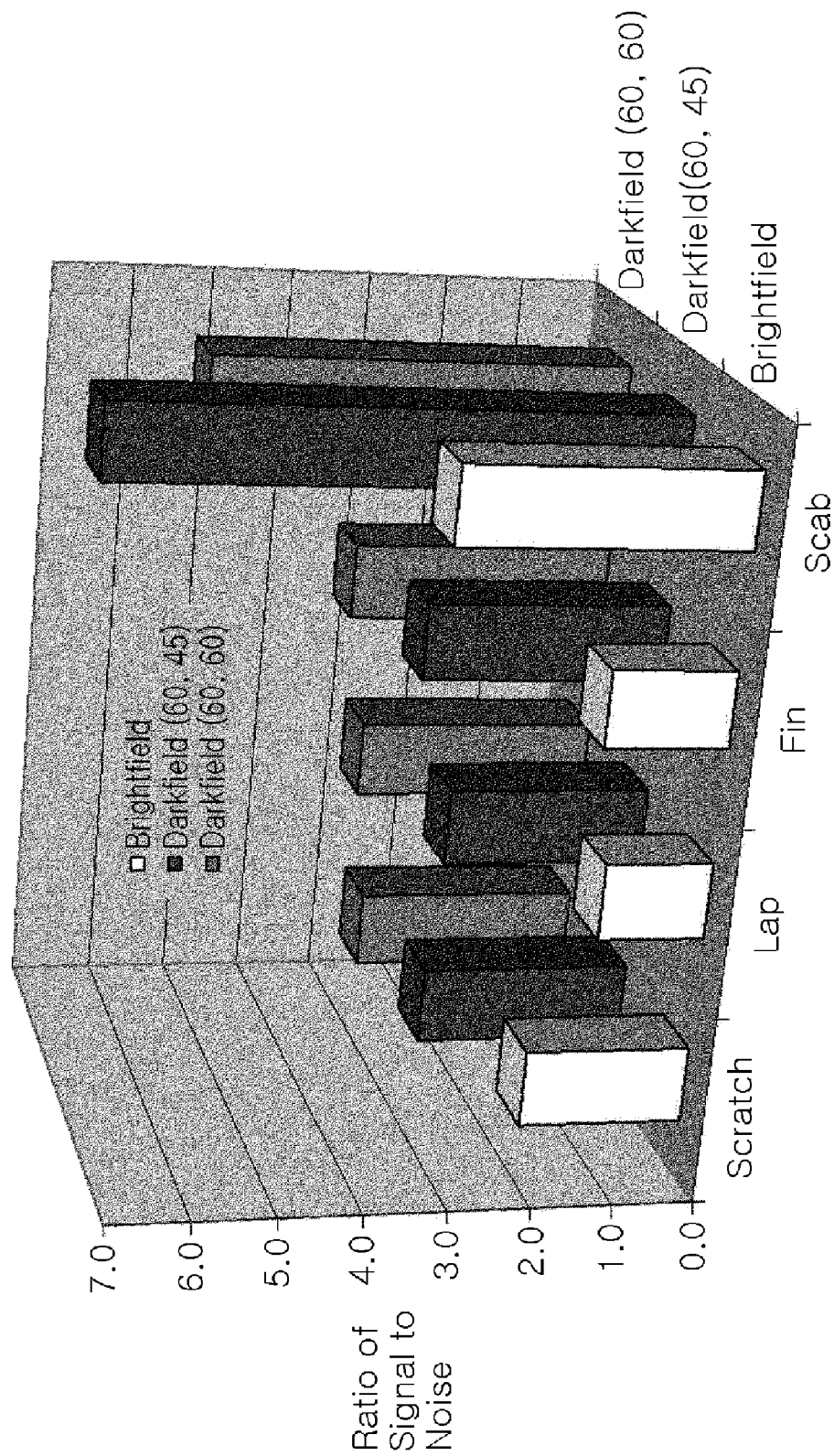
FIG. 19 is a graph illustrating ratios of signal to noise measured from scratch, fin, lap and scab defects on the surface of the round wire rod according to emission angles.

In U.S. Pat. No. 6,950,546, as shown in FIG. 13, the angle between the optical sensor 13 and the lighting device 3 is set 1° or less, thereby forming a bright field. In the present invention, as shown in FIG. 14, the optical sensor 13 is arranged along the vertical radial direction of the round wire rod 2, and the emission direction of the external lighting device 17 is set to form a dark field by increasing an angle $\alpha$ with respect to a perpendicular of the transporting direction of the round wire rod 2, and is set to form a double dark field by increasing an angle $\beta$ with respect to the vertical radial direction of the round wire rod 2. The results of defect detection performances (i.e., ratios of signal to noise) can be seen from FIG. 19. From the results of FIG. 19, it can be appreciated that the defect detection performances (i.e., ratios of signal to noise) are excellent in the double dark field of the present invention that in the bright field of U.S. Pat. No. 6,950,546. In FIG. 19, Darkfield (60, 45) and Darkfield (60, 45) indicate ($\alpha$, $\beta$).

Figure 20:
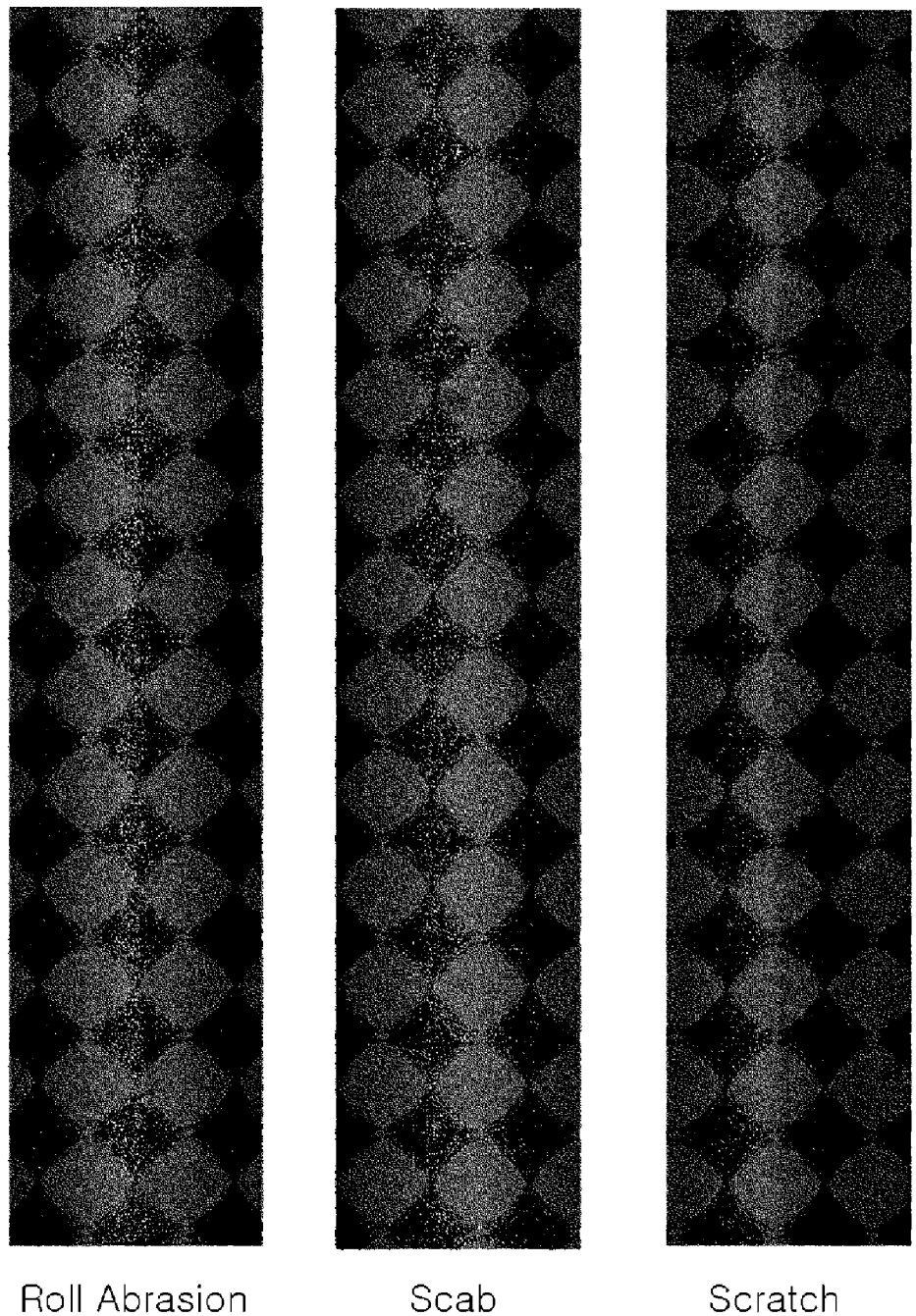
FIG. 20 is a view illustrating images of the scratch, fin, lap and scab defects acquired using the device for detecting a surface defect of a hot round wire rod according to the present invention.
Figure 21:
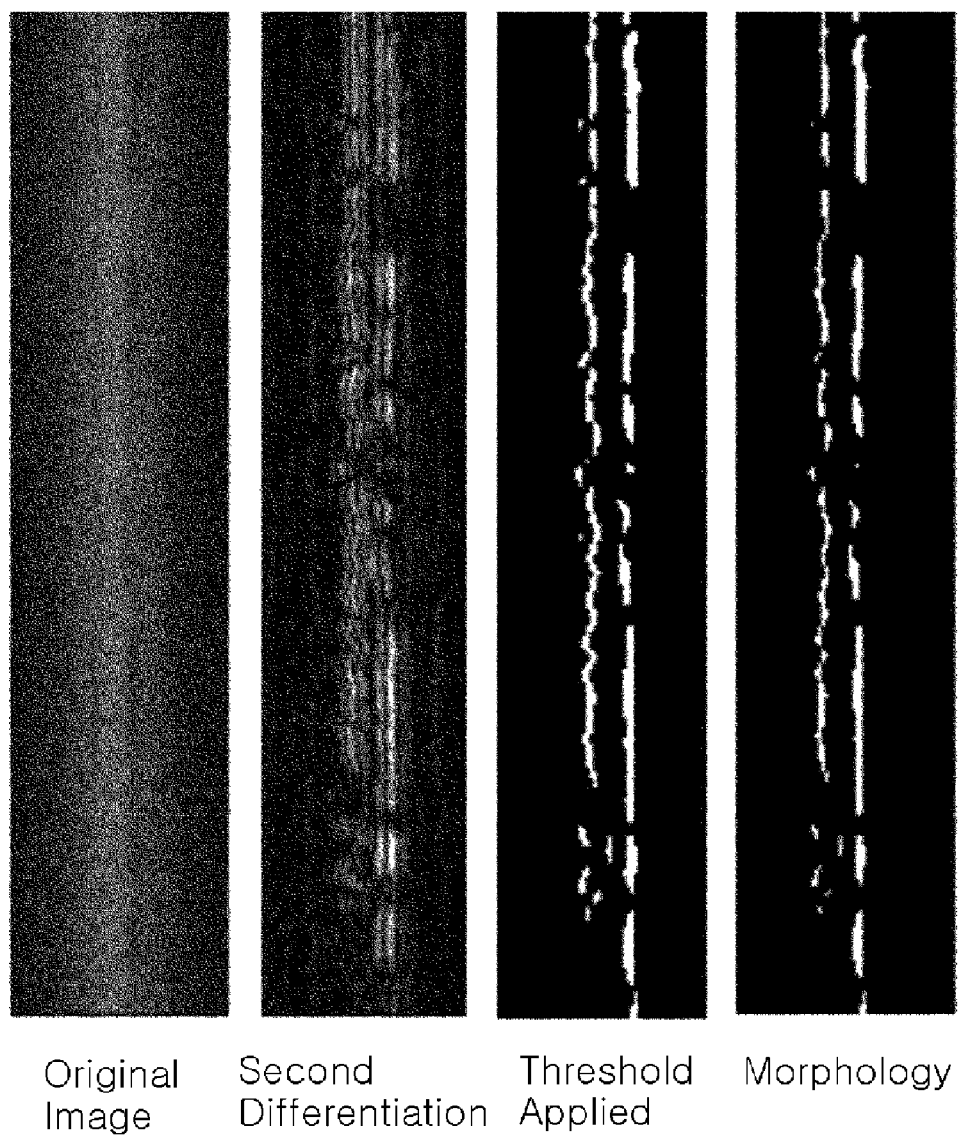
FIG. 21 is a view illustrating images of a process of optically detecting defects in the case of the roll abrasion of FIG. 20.
Figure 22:
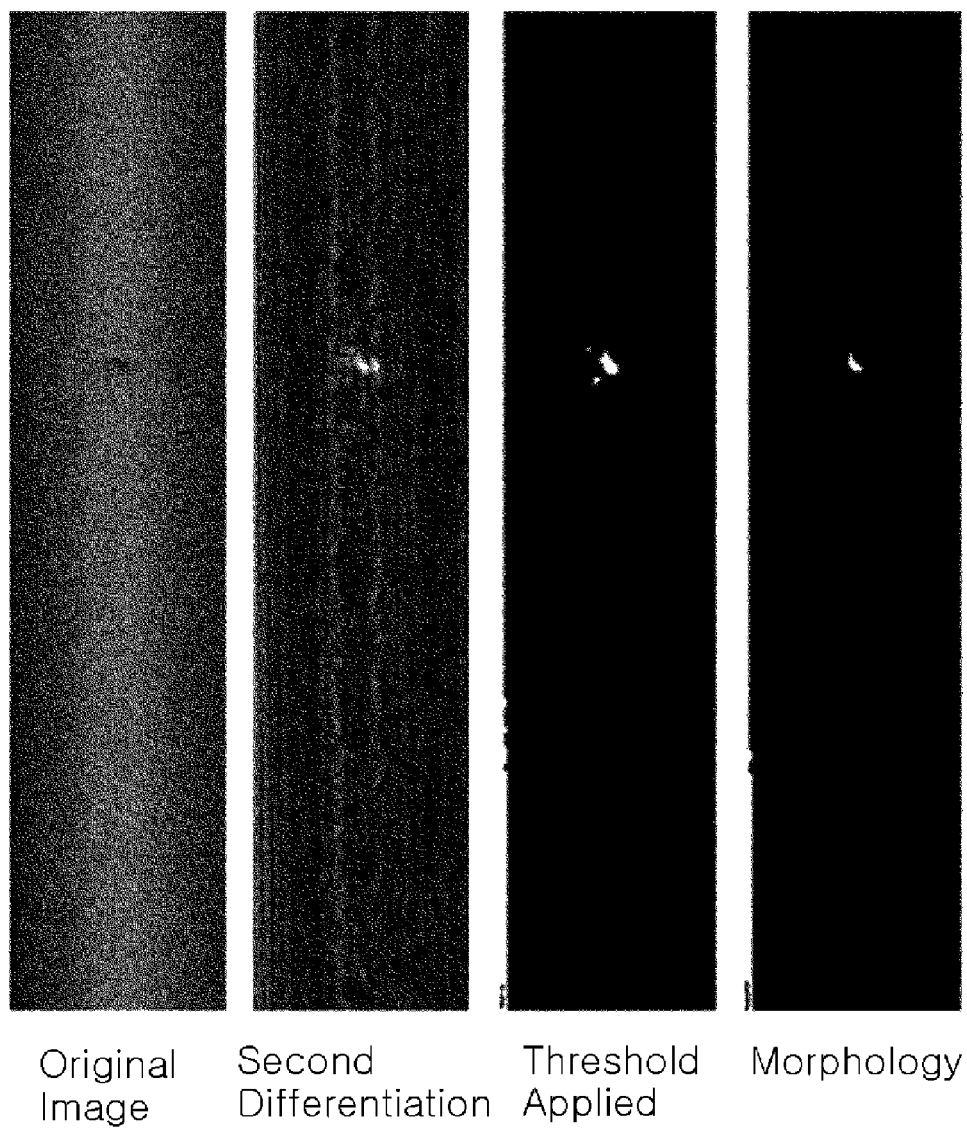
FIG. 22 is a view illustrating images of a process of optically detecting defects in the case of the scab defect of FIG. 20.
Figure 23:
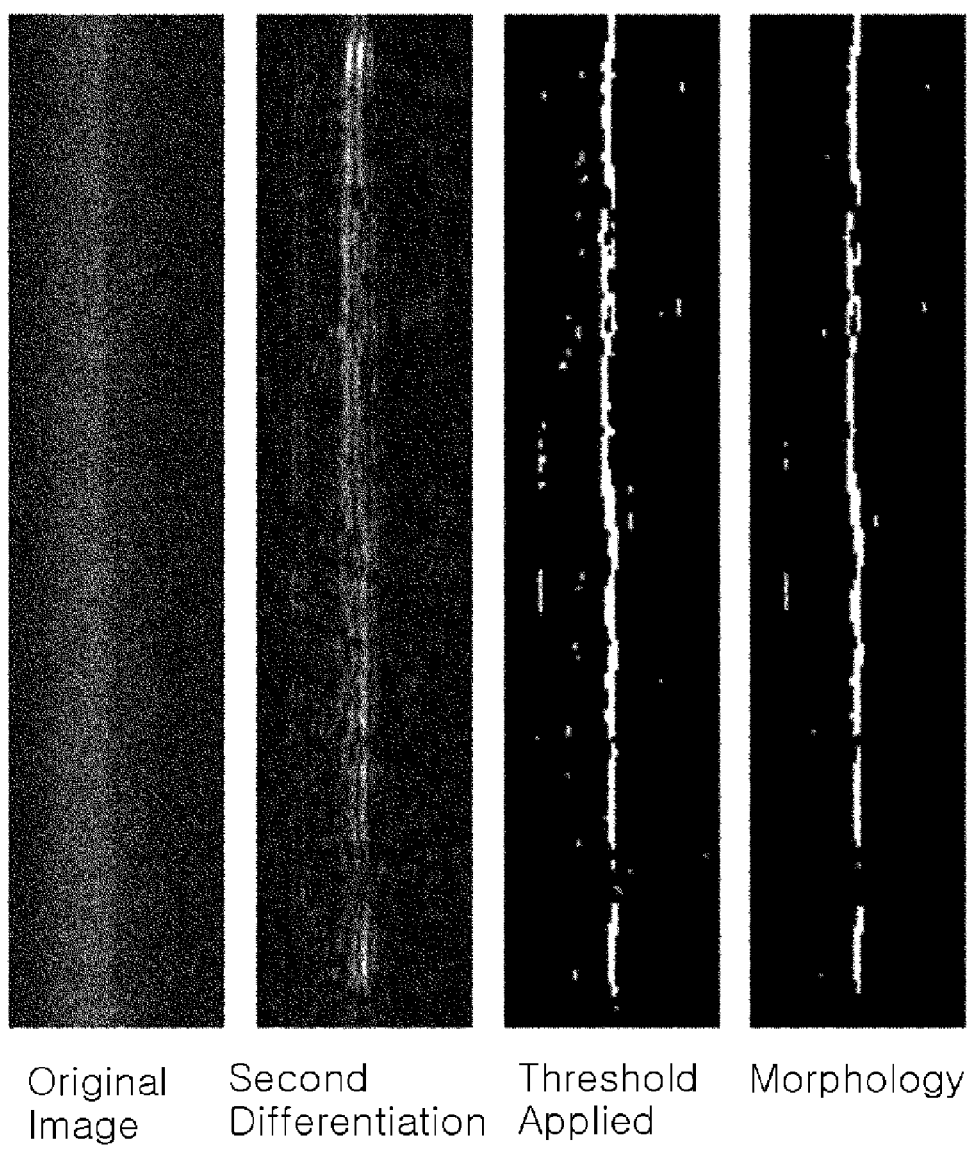
FIG. 23 is a view illustrating images of a process of optically detecting defects in the case of the scratch defect of FIG. 20.

FIG. 20 shows original images of optical defects such as roll abrasion, scab and scratch, which were acquired using the device for detecting a defect of a round wire rod. Then, each of the images was subjected to second-order partial differentiation, applied with a threshold, and subjected to morphological processing. The resultant images are shown in FIGS. 21, 22 and 23, respectively. Referring to FIGS. 21 to 23, it can be appreciated that actual images are substantially identical with those produced by the method for detecting a defect of a round wire rod. Regarding times required for performing a defect-detecting algorithm from 512×512 pixel images, 3.4 ms was spent for the original images, the second-order partial differentiation, the application of threshold and the morphology processing, and 0.67 ms was spent for application of moving average. When the optical sensor acquiring linear images along the transporting direction of the round wire rod has a pixel of 0.3 mm on the surface of the round wire rod, optical defect inspection can be performed under 50% of a required processing time. Accordingly, the device can detect a defect on the surface of a round wire rod in real-time, wherein the defect is manufactured with a diameter 14 mm or more and a maximum length 18 m per second.

Figure 24:
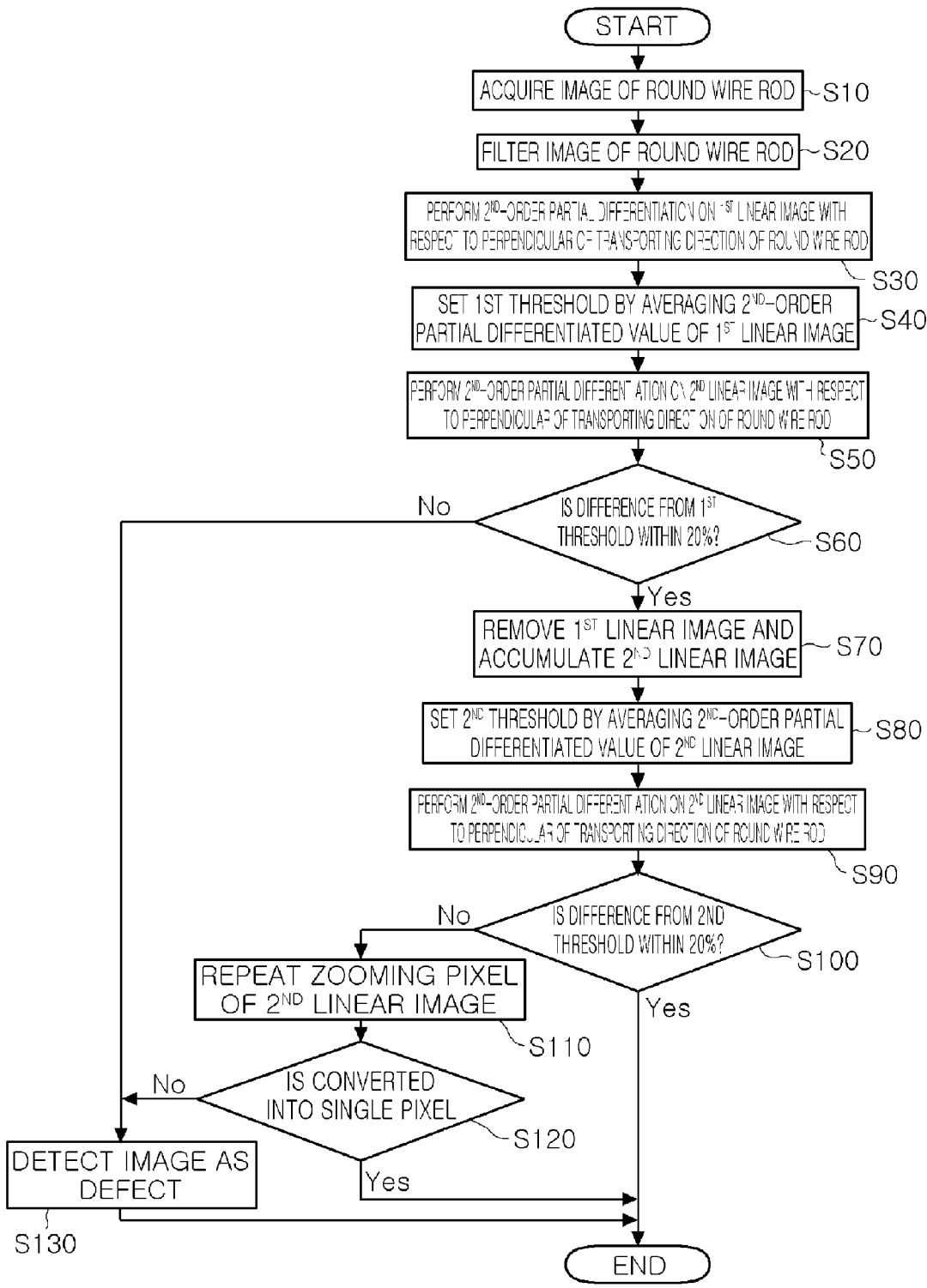
FIG. 24 is a flowchart illustrating a method for optically detecting a defect of a round wire rod according to the present invention.

The method for optically detecting a surface defect of a round wire rod will be described below in detail with reference to FIG. 24.

First, a signal-processing unit acquires an image of the round wire rod from an optical sensor (S10). The optical sensor generates an optical signal from reflective light of the lighting device which is reflected from the round wire rod, and then converts the generated optical signal into an image signal. Thereby, the signal-processing unit obtains the image of the round wire rod. Typically, the optical sensor employs a linear charge coupled device (CCD) optical sensor.

Afterwards, the signal-processing unit filters the image of the round wire rod (S20). The reason of filtering the image of the round wire rod is for removing fine noises from the image to thereby obtain clear edges of a defect. To this end, a Gaussian smoothing filter is used.

Then, the signal-processing unit performs second-order partial differentiation on a first linear image acquired in the direction perpendicular to the transporting direction of the round wire rod (S30). Since the round wire rod formed continuously has a lengthwise defect, such partial differentiation serves to further clarify lengthwise characteristics of the defect.

Subsequently, the signal-processing unit averages second-order partial differentiation values of the first linear image to set a first threshold (S40). This is for making it possible to follow reflective characteristics varying in the transporting direction of the round wire rod. For example, the second-order partial differentiation values of continuously received twenty (20) lines are averaged, and then the averaged value is set as the first threshold.

Now, the signal-processing unit performs second-order partial differentiation on a second linear image acquired in the direction perpendicular to a transporting direction of the round wire rod (S50). Similar to the process S30, since the round wire rod formed continuously has lengthwise defect, such partial differentiation serves to further clarify lengthwise characteristics of the defect.

Then, it is determined whether or not a difference between each second-order partial differentiation value of the second linear image and the first threshold is within a predetermined range (S60). If a difference between each second-order partial differentiation value of the second linear image and the first threshold is within a predetermined range, the signal-processing unit removes the first linear image, and then accumulates the second linear image (S70). This process is a process of substituting the second-order partial differentiation values of the process S30 with the second-order partial differentiation of the process S50. Generally, if the difference between each second-order partial differentiation value of the linear image and the threshold is within 20%, it is determined that the image has good pixels. In contrast, if the difference between each second-order partial differentiation value of the linear image and the threshold is beyond 20%, it is determined that the image has bad pixels.

Then, the signal-processing unit averages second-order partial differentiation values of the second linear image to set a second threshold (S80). Similar to the process S40, this is for making it possible to follow reflective characteristics varying in the transporting direction of the round wire rod. For example, the second-order partial differentiation values of continuously received 20 lines are averaged, and then the averaged value is set as the second threshold.

Now, the signal-processing unit performs second-order partial differentiation on the second linear image acquired in the direction perpendicular to a transporting direction of the round wire rod (S90). Similar to the process S50, since the round wire rod formed continuously has the lengthwise defect, such partial differentiation serves to further clarify lengthwise characteristics of the defect.

Then, it is determined whether or not a difference between each second-order partial differentiation value of the second linear image and the second threshold is within a predetermined range (S100). If a difference between each second-order partial differentiation value of the second linear image and the second threshold is not within a predetermined range, the signal-processing unit repeats zooming up and down the pixels of the second linear image up to a predetermined number of times (S110).

Then, it is determined whether or not the second linear image pixels are converted into a single pixel (S120). If the second linear image pixels are not converted into a single pixel, the signal-processing unit detects the second linear image pixels as bad pixels (S130).

If the difference between each second-order partial differentiation value of the second linear image and the first threshold is not within a predetermined range in the process S60, the signal-processing means detects the image pixels as bad pixels.

Further, if the difference between each second-order partial differentiation value of the second linear image and the second threshold is within a predetermined range in the process S100, or if the second linear image pixels are converted into a single pixel in the process S120, the signal-processing unit does not detect the image pixels as bad pixels.

The invention claimed is:

1. A method for optically detecting a defect of a round wire rod, comprising:
   acquiring an image of the round wire rod from an optical sensor, and filtering the acquired image;
   performing second-order partial differentiation on a first linear image acquired in the direction perpendicular to a transporting direction of the round wire rod, averaging second-order partial differentiation values of the first linear image, and setting the averaged value as a first threshold;
   performing second-order partial differentiation on a second linear image acquired in the direction perpendicular to the transporting direction of the round wire rod, and removing the first linear image and accumulating the second linear image if a difference between each second-order partial differentiation value of the first linear image and the first threshold is within a predetermined range;
   averaging second-order partial differentiation values of the second linear image, and setting the averaged value as a second threshold;
   performing second-order partial differentiation on a second linear image acquired in the direction perpendicular to the transporting direction of the round wire rod, and repeating zooming of pixels of the second linear image up to a predetermined number of times if a difference between each second-order partial differentiation value of the second linear image and the second threshold is within a predetermined range; and
   detecting the second linear image pixels as had pixels if the second linear image pixels are not converted into a single pixel.

* * * * *

UNITED STATES PATENT AND TRADEMARK OFFICE
CERTIFICATE OF CORRECTION

PATENT NO. : 8,306,308 B2  
APPLICATION NO. : 12/675405  
DATED : November 6, 2012  
INVENTOR(S) : Se Ho Choi et al.

Page 1 of 1

It is certified that error appears in the above-identified patent and that said Letters Patent is hereby corrected as shown below:

Column 16, Line 47, Claim 1, delete "had" and insert -- bad --

Signed and Sealed this
Twelfth Day of February, 2013

Teresa Stanek Rea
*Acting Director of the United States Patent and Trademark Office*